US008389493B2

(12) United States Patent
Brown et al.

(10) Patent No.: US 8,389,493 B2
(45) Date of Patent: *Mar. 5, 2013

(54) MICROSPHERE-BASED COMPOSITION FOR PREVENTING AND/OR REVERSING NEW-ONSET AUTOIMMUNE DIABETES

(75) Inventors: Larry R. Brown, Newton, MA (US); Nick Giannoukakis, Coraopolis, PA (US); Kimberly A. Gillis, Beverly, MA (US); Massimo Trucco, Pittsburgh, PA (US)

(73) Assignees: Baxter International Inc., Deerfield, IL (US); Baxter Healthcare SA, Glattpark (Opfikon) (CH); University of Pittsburgh—of The Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/103,433

(22) Filed: May 9, 2011

(65) Prior Publication Data
US 2011/0274758 A1 Nov. 10, 2011

Related U.S. Application Data

(62) Division of application No. 11/834,550, filed on Aug. 6, 2007, now Pat. No. 7,964,574.

(60) Provisional application No. 60/835,742, filed on Aug. 4, 2006, provisional application No. 60/864,914, filed on Nov. 8, 2006.

(51) Int. Cl.
*A61K 48/00* (2006.01)
(52) U.S. Cl. ...... 514/44; 536/24.5; 536/24.31; 536/24.1
(58) Field of Classification Search .......... None
See application file for complete search history.

(56) References Cited

U.S. PATENT DOCUMENTS

| | | | |
|---|---|---|---|
| 3,737,337 A | 6/1973 | Schnoring et al. |
| 3,891,570 A | 6/1975 | Fukushima et al. |
| 4,389,330 A | 6/1983 | Tice et al. |
| 4,530,840 A | 7/1985 | Tice et al. |
| 4,584,894 A | 4/1986 | Fogelberg |
| 4,652,441 A | 3/1987 | Okada et al. |
| 4,728,721 A | 3/1988 | Yamamoto et al. |
| 4,818,542 A | 4/1989 | DeLuca et al. |
| 4,849,228 A | 7/1989 | Yamamoto et al. |
| 4,861,627 A | 8/1989 | Mathiowitz et al. |
| 4,897,268 A | 1/1990 | Tice et al. |
| 4,904,479 A | 2/1990 | Illum |
| 4,917,893 A | 4/1990 | Okada et al. |
| 5,075,109 A | 12/1991 | Tice et al. |
| 5,102,872 A | 4/1992 | Singh et al. |
| 5,149,543 A | 9/1992 | Cohen et al. |
| 5,213,812 A | 5/1993 | Ruiz |
| 5,300,464 A | 4/1994 | Rittler |
| 5,330,767 A | 7/1994 | Yamamoto et al. |
| 5,330,768 A | 7/1994 | Park et al. |
| 5,360,610 A | 11/1994 | Tice et al. |
| 5,384,133 A | 1/1995 | Boyes et al. |
| 5,407,609 A | 4/1995 | Tice et al. |
| 5,417,986 A | 5/1995 | Reid et al. |
| 5,422,120 A | 6/1995 | Kim |
| 5,476,663 A | 12/1995 | Okada et al. |
| 5,480,656 A | 1/1996 | Okada et al. |
| 5,525,519 A | 6/1996 | Woiszwillo |
| 5,543,158 A | 8/1996 | Gref et al. |
| 5,554,730 A | 9/1996 | Woiszwillo et al. |
| 5,556,642 A | 9/1996 | Kobayashi et al. |
| 5,575,987 A | 11/1996 | Kamei et al. |
| 5,578,709 A | 11/1996 | Woiszwillo |
| 5,599,719 A | 2/1997 | Woiszwillo et al. |
| 5,603,961 A | 2/1997 | Suzuki et al. |
| 5,620,883 A | 4/1997 | Shao et al. |
| 5,631,020 A | 5/1997 | Okada et al. |
| 5,631,021 A | 5/1997 | Okada et al. |
| 5,643,607 A | 7/1997 | Okada et al. |
| 5,650,173 A | 7/1997 | Ramstack et al. |
| 5,654,008 A | 8/1997 | Herbert et al. |
| 5,654,010 A | 8/1997 | Johnson et al. |
| 5,665,428 A | 9/1997 | Cha et al. |
| 5,667,808 A | 9/1997 | Johnson et al. |
| 5,716,640 A | 2/1998 | Kamei et al. |
| 5,851,451 A | 12/1998 | Takechi et al. |
| 5,891,478 A | 4/1999 | Johnson et al. |
| 5,932,248 A | 8/1999 | Chen et al. |
| 5,945,126 A | 8/1999 | Thanoo et al. |
| 5,972,707 A | 10/1999 | Roy et al. |
| 5,981,719 A | 11/1999 | Woiszwillo et al. |
| 5,989,463 A | 11/1999 | Tracy et al. |
| 5,994,314 A | 11/1999 | Eljamal et al. |

(Continued)

FOREIGN PATENT DOCUMENTS

| | | |
|---|---|---|
| DE | 04312970 | 10/1994 |
| DE | 19812083 | 9/1999 |

(Continued)

OTHER PUBLICATIONS

Ahn et al., Biodegradable poly(ethylenimine) for plasmid DNA delivery, *J. Control. Rel.*, 80:273-282 (2002).

(Continued)

*Primary Examiner* — Kimberly Chong
(74) *Attorney, Agent, or Firm* — Marshall, Gerstein & Borun, LLP

(57) ABSTRACT

AS-oligonucleotides are delivered in microsphere form in order to induce dendritic cell tolerance, particularly in the non-obese-diabetic (NOD) mouse model. The microspheres incorporate antisense (AS) oligonucleotides. A process includes using an antisense approach to reverse an autoimmune diabetes condition in NOD mice in vivo. The oligonucleotides are targeted to bind to primary transcripts CD40, CD80, CD86 and their combinations.

10 Claims, 16 Drawing Sheets

U.S. PATENT DOCUMENTS

| | | | |
|---|---|---|---|
| 6,020,175 A | 2/2000 | Onda et al. | |
| 6,036,976 A | 3/2000 | Takechi et al. | |
| 6,048,550 A | 4/2000 | Chan et al. | |
| 6,051,228 A * | 4/2000 | Aruffo et al. | 424/144.1 |
| 6,051,259 A | 4/2000 | Johnson et al. | |
| 6,063,910 A | 5/2000 | Debenedetti et al. | |
| 6,077,833 A | 6/2000 | Bennett et al. | |
| 6,090,925 A | 7/2000 | Woiszwillo et al. | |
| 6,107,084 A | 8/2000 | Onda et al. | |
| 6,120,787 A | 9/2000 | Gustafsson et al. | |
| 6,140,475 A | 10/2000 | Margolin et al. | |
| 6,153,211 A | 11/2000 | Hubbell et al. | |
| 6,197,584 B1 | 3/2001 | Bennett et al. | |
| 6,242,230 B1 | 6/2001 | Batich et al. | |
| 6,252,055 B1 | 6/2001 | Relton et al. | |
| 6,265,389 B1 | 7/2001 | Burke | |
| 6,267,958 B1 | 7/2001 | Andya et al. | |
| 6,268,053 B1 | 7/2001 | Woiszwillo et al. | |
| 6,270,795 B1 | 8/2001 | Jones et al. | |
| 6,270,802 B1 | 8/2001 | Thanoo et al. | |
| 6,290,991 B1 | 9/2001 | Roser et al. | |
| 6,303,582 B1 | 10/2001 | Eljamal et al. | |
| 6,312,727 B1 | 11/2001 | Schacht et al. | |
| 6,319,906 B1 | 11/2001 | Bennett et al. | |
| 6,361,798 B1 | 3/2002 | Thanoo et al. | |
| 6,395,253 B2 | 5/2002 | Levy et al. | |
| 6,395,302 B1 | 5/2002 | Hennink et al. | |
| 6,455,074 B1 | 9/2002 | Tracy et al. | |
| 6,458,387 B1 | 10/2002 | Scott et al. | |
| 6,475,995 B1 | 11/2002 | Roy et al. | |
| 6,479,146 B1 | 11/2002 | Caruso et al. | |
| 6,500,448 B1 | 12/2002 | Johnson et al. | |
| 6,506,410 B1 | 1/2003 | Park et al. | |
| 6,534,483 B1 | 3/2003 | Bruno et al. | |
| 6,541,606 B2 | 4/2003 | Margolin et al. | |
| 6,569,458 B1 | 5/2003 | Gombotz et al. | |
| 6,596,316 B2 | 7/2003 | Lyons et al. | |
| 6,616,949 B2 | 9/2003 | Jonsson et al. | |
| 6,630,169 B1 | 10/2003 | Bot et al. | |
| 6,645,525 B1 | 11/2003 | Woiszwillo et al. | |
| 6,699,501 B1 | 3/2004 | Neu et al. | |
| 6,713,533 B1 | 3/2004 | Panzner et al. | |
| 6,749,866 B2 | 6/2004 | Bernstein et al. | |
| 6,814,980 B2 | 11/2004 | Levy et al. | |
| 6,830,737 B2 | 12/2004 | Ramstack | |
| 6,833,192 B1 | 12/2004 | Caruso et al. | |
| 6,849,259 B2 | 2/2005 | Haurum et al. | |
| 6,861,064 B1 | 3/2005 | Laakso et al. | |
| 6,875,432 B2 | 4/2005 | Liu et al. | |
| 7,378,095 B2 | 5/2008 | Cao et al. | |
| 2001/0002261 A1 | 5/2001 | Morrison et al. | |
| 2002/0009453 A1 | 1/2002 | Haurum et al. | |
| 2002/0045571 A1 | 4/2002 | Liu et al. | |
| 2002/0136719 A1 | 9/2002 | Shenoy et al. | |
| 2002/0137156 A1 | 9/2002 | Margolin et al. | |
| 2002/0146459 A1 | 10/2002 | Levy et al. | |
| 2002/0187197 A1 | 12/2002 | Caruso et al. | |
| 2002/0197325 A1 | 12/2002 | Osborne | |
| 2003/0007990 A1 | 1/2003 | Blankenship et al. | |
| 2003/0026844 A1 | 2/2003 | Lee et al. | |
| 2003/0059474 A1 | 3/2003 | Scott et al. | |
| 2003/0124368 A1 | 7/2003 | Lynn et al. | |
| 2003/0129239 A1 | 7/2003 | Goldshtein | |
| 2003/0137067 A1 | 7/2003 | Cooper et al. | |
| 2003/0157181 A1 | 8/2003 | Panzner et al. | |
| 2003/0175239 A1 | 9/2003 | Margolin et al. | |
| 2003/0180370 A1 | 9/2003 | Lesniak et al. | |
| 2003/0211153 A1 | 11/2003 | Johnson et al. | |
| 2003/0236214 A1 | 12/2003 | Wolff et al. | |
| 2004/0013721 A1 | 1/2004 | Antipov et al. | |
| 2004/0013738 A1 | 1/2004 | Voigt et al. | |
| 2004/0014698 A1 | 1/2004 | Hortelano et al. | |
| 2004/0017018 A1 | 1/2004 | Pommersheim | |
| 2004/0022081 A1 | 2/2004 | Erickson et al. | |
| 2004/0043076 A1 | 3/2004 | Dulieu et al. | |
| 2004/0047979 A1 | 3/2004 | Qiu et al. | |
| 2004/0110898 A1 | 6/2004 | Dreja et al. | |
| 2004/0185091 A1 | 9/2004 | Truong et al. | |
| 2004/0186071 A1 | 9/2004 | Bennett et al. | |
| 2004/0197324 A1 | 10/2004 | Liu et al. | |
| 2004/0202643 A1 | 10/2004 | Margolin et al. | |
| 2004/0209804 A1 | 10/2004 | Govardhan et al. | |
| 2004/0219224 A1 | 11/2004 | Yakovlevsky et al. | |
| 2004/0241202 A1 | 12/2004 | Chluba et al. | |
| 2004/0258762 A1 | 12/2004 | Boppart et al. | |
| 2005/0048127 A1 | 3/2005 | Brown et al. | |
| 2005/0053666 A1 | 3/2005 | Tzannis et al. | |
| 2005/0142201 A1 | 6/2005 | Rashba-Step et al. | |
| 2005/0142205 A1 | 6/2005 | Rashba-Step et al. | |
| 2005/0142206 A1 | 6/2005 | Brown et al. | |
| 2005/0147687 A1 | 7/2005 | Rashba-Step et al. | |
| 2005/0158303 A1 | 7/2005 | Liu et al. | |
| 2005/0170005 A1 | 8/2005 | Rashba-Step et al. | |
| 2005/0175603 A1 | 8/2005 | Liu et al. | |
| 2005/0180967 A1 | 8/2005 | Haurum et al. | |
| 2005/0202072 A1 | 9/2005 | Buch-Rasmussen et al. | |
| 2005/0233945 A1 | 10/2005 | Brown et al. | |
| 2005/0271732 A1 | 12/2005 | Seeney et al. | |
| 2006/0002862 A1 | 1/2006 | Truong-Le et al. | |
| 2006/0018971 A1 | 1/2006 | Scott et al. | |
| 2006/0024240 A1 | 2/2006 | Brown et al. | |
| 2006/0024379 A1 | 2/2006 | Brown et al. | |
| 2006/0127395 A1 | 6/2006 | Arvinte et al. | |
| 2006/0182740 A1 | 8/2006 | Yang et al. | |
| 2006/0276425 A1 | 12/2006 | Mourich et al. | |
| 2007/0023776 A1 | 2/2007 | Zakgeym et al. | |
| 2007/0065440 A1 | 3/2007 | Tomlinson et al. | |
| 2007/0122411 A1 | 5/2007 | Matheus et al. | |
| 2007/0161589 A1 | 7/2007 | Bennett et al. | |
| 2007/0172475 A1 | 7/2007 | Matheus et al. | |
| 2007/0172479 A1 | 7/2007 | Warne et al. | |

FOREIGN PATENT DOCUMENTS

| | | |
|---|---|---|
| DE | 10157799 | 9/2002 |
| EP | 0248531 | 12/1987 |
| EP | 0377477 | 7/1990 |
| EP | 0564061 | 10/1993 |
| EP | 0647477 | 4/1995 |
| EP | 0809110 | 11/1997 |
| EP | 0936902 | 8/1999 |
| EP | 0957926 | 11/1999 |
| EP | 0972563 | 1/2000 |
| EP | 1060741 | 12/2000 |
| EP | 1116516 | 7/2001 |
| EP | 1173151 | 1/2002 |
| EP | 1173550 | 1/2002 |
| EP | 0975334 | 2/2002 |
| EP | 1283720 | 2/2003 |
| EP | 1801123 | 6/2004 |
| EP | 1614751 | 1/2006 |
| EP | 0907378 | 2/2006 |
| JP | 08245815 | 9/1996 |
| JP | 2006219455 | 8/2006 |
| WO | WO-91/07951 | 6/1991 |
| WO | WO-93/14110 | 7/1993 |
| WO | WO-94/18947 | 9/1994 |
| WO | WO-94/20856 | 9/1994 |
| WO | WO-94/24263 | 10/1994 |
| WO | WO-95/00128 | 1/1995 |
| WO | WO-96/03978 | 2/1996 |
| WO | WO-96/08289 | 3/1996 |
| WO | WO-97/45140 | 12/1997 |
| WO | WO-99/47252 | 9/1999 |
| WO | WO-99/47253 | 9/1999 |
| WO | WO-00/03797 | 1/2000 |
| WO | WO-00/28972 | 5/2000 |
| WO | WO-00/41679 | 7/2000 |
| WO | WO-00/62759 | 10/2000 |
| WO | WO-00/77281 | 12/2000 |
| WO | WO-01/28524 | 4/2001 |
| WO | WO-01/51196 | 7/2001 |
| WO | WO-01/64330 | 9/2001 |
| WO | WO-01/89563 | 11/2001 |
| WO | WO-02/09864 | 2/2002 |
| WO | WO-02/09865 | 2/2002 |
| WO | WO-02/17888 | 3/2002 |
| WO | WO-02/072636 | 9/2002 |

| | | |
|---|---|---|
| WO | WO-02/074431 | 9/2002 |
| WO | WO-02/096457 | 12/2002 |
| WO | WO-03/000014 | 1/2003 |
| WO | WO-03/015750 | 2/2003 |
| WO | WO-03/030874 | 4/2003 |
| WO | WO-03/043729 | 5/2003 |
| WO | WO-03/087384 | 10/2003 |
| WO | WO-03/090920 | 11/2003 |
| WO | WO-03/097706 | 11/2003 |
| WO | WO-03/099228 | 12/2003 |
| WO | WO-2004/001007 | 12/2003 |
| WO | WO-2004/030649 | 4/2004 |
| WO | WO-2004/058156 | 7/2004 |
| WO | WO-2004/060343 | 7/2004 |
| WO | WO-2004/060920 | 7/2004 |
| WO | WO-2004/100928 | 11/2004 |
| WO | WO-2005/035088 | 4/2005 |
| WO | WO-2005/051355 | 6/2005 |
| WO | WO-2005/077414 | 8/2005 |
| WO | WO-2005/008443 | 9/2005 |
| WO | WO-2005/089727 | 9/2005 |
| WO | WO-2005/112885 | 12/2005 |
| WO | WO-2005/112893 | 12/2005 |
| WO | WO-2005/112894 | 12/2005 |
| WO | WO-2005/123131 | 12/2005 |
| WO | WO-2006/031560 | 3/2006 |
| WO | WO-2006/065746 | 6/2006 |
| WO | WO-2006/072527 | 7/2006 |
| WO | WO-2006/112838 | 10/2006 |
| WO | WO-2007/031333 | 3/2007 |
| WO | WO-2007/076062 | 7/2007 |

OTHER PUBLICATIONS

Al et al., Nano-encapsulation of furosemid microcrystals for controlled drug release, *J. Control. Rel.*, 86:59-68 (2003).
Akhtar et al., Antisense oligonucleotide delivery to cultured macrophages is improved by incorporation into sustained-release biodegradable polymer microspheres. *Int. J. Pharma.*, 151: 57-67 (1997).
Ariga et al., Self-assembly of functional protein multilayers: from planar films to microtemplate encapsulation, pp. 367-391, IN: Malmsten (ed.), *Biopolymers at Interfaces*, 2nd ed., Marcel Dekker (2003).
Banchereau et al., Dendritic cells and the control of immunity, *Nature*, 392:245-252 (1998).
Berton et al., Improved oligonucleotide uptake and stability by a new drug carrier, the supramolecular bio vector (SMBV), *Biochim. Biophys. Acta*, 1355:7-19 (1997).
Bisker-Leib et al., Factor VII monoclonal antibody microspheres, IN: *Proc. 2004 Am. Assoc. Pharm. Scientists Natl. Biotech. Conf.*, p. 76 (2004).
Bisker-Leib et al., Uniform microsphere formation from small organic molecules, *Transactions, 31st Ann. Meeting Control. Release Soc.*, #631A (2004).
Boussif et al., A versatile vector for gene and oligonucleotide transfer into cells in culture and in vivo: polyethylenimine, *Proc. Natl. Acad. Sci. USA*, 92:7297-7301 (1995).
Brazeau et al., In vitro myotoxicity of selected cationic macromolecules used in non-viral gene delivery, *Pharm. Res.*, 15:680-684 (1998).
Brown et al., PROMAXX microsphere characterization, *Respiratory Drug Delivery IX*, 2:477-479 (2004).
Brown et al., Pulmonary delivery of novel insulin microspheres, *Respiratory Drug Delivery VIII*, 2:431-434 (2002).
Bustami et al., Generation of micro-particles of proteins for aerosol delivery using high pressure modified carbon dioxide, *Pharm. Res.*, 17:1360-1366 (2000).

Byrne et al., Dendritic cells: making progress with tumour regression? *Immunol. Cell Biol.*, 80:520-530 (2002).

Chamarthy et al., A cationic peptide consists of ornithine and histidine repeats augments gene transfer in dendritic cells, *Mol. Immunol.*, 40:483-490 (2003).

Check, A tragic setback, *Nature*, 420:116-118 (2002).

Chollet et al., Side-effects of a systemic injection of linear polythylenimine-DNA complexes, *J. Gene Med.*, 41:84-91 (2002).

Chu et al., Efficiency of cytoplasmic delivery by pH-sensitive liposomes to cells in culture, *Pharm. Res.*, 7:824-834 (1990).

Couvreur et al., pH-sensitive liposomes: an intelligent design system for the delivery of antisense oligonucleotides, *J. Liposome Res.*, 7:1-18 (1997).

Crystal, Transfer of genes to humans: early lessons and obstacles for success, *Science*, 270:404-410 (1995).

De Rosa et al., A new delivery system for antisense therapy: PLGA microspheres encapsulating oligonucleotide/polyethyleimine solid complexes. *Int. J. Pharmaceut.*, 254: 89-93 (2003).

Dokka et al., Inhibition of endotoxin-induced lung inflammation by interleukin-10 gene transfer in mice, *Am. J. Physiol. Lung Cell Mol. Physiol.*, 279:L872-L877 (2000).

Eliassi et al., Densities of poly(ethylene glycol) + water mixtures in the 298. 15-328.15 K temperature, *J. Chem. Eng. Data*, 43:719-721 (1998).

Felgner et al., Cationic liposome-mediated transfection, *Nature*, 337:387-388 (1989).

Gao et al., CD4-deficient dendritic cells producing interleukin-10 but not interleukin-12 induce T-cell hyporesponsiveness in vitro and prevent acute allograft rejection. *Immunology*, 98: 159-170 (1991).

Glorioso et al., Development of herpes simplex virus vectors for gene transfer to the central nervous system, pp. 281-302, IN: WOLFF (ed.), *Gene Therapeutics: Methods and Applications of Direct Gene Transfer* (1993).

Govardhan et al., Novel long-acting crystal formulation of human growth hormone, *Pharm. Res.*, 22:1461-1470 (2005).

Hudson et al., Biodegradable polymer matrices for the sustained exogenous delivery of a biologically active c-myc hammerhead ribozymes, *Int. J. Pharm.*, 136:23-29 (1996).

Hughes et al., Evaluation of adjuvants that enhance the effectiveness of antisense oligodeoxynucleotides, *Pharm. Res.*, 13:404-410 (1996).

Hwang et al., Cationic polymers for gene delivery: designs for overcoming barriers to systemic administration, *Curr. Opin. Mol. Ther.*, 3:183-191 (2001).

Kabanov et al., Water-soluble block polycations as carriers for oligonucleotide delivery, *Bioconjugate Chem.*, 6:639-643 (1995).

Kataoka et al., Spontaneous formation of polyion complex micelles with narrow distribution from antisense oligonucleotide and cationic block copolymer in physiological saline, *Macromolecules*, 29:8556-8557 (1996).

Larionova et al., Encapsulation of proteins in polyelectrolyte microcapsules. Factors regulating the protein release, *Proc. Intl. Symp. Control. Release Bloact. Mater.*, 28:1398-1399 (2001).

Leaversuch, Materials renewable PLA polymer gets 'green light' for packaging uses. pp. 1-4. Retrieved from the Internet Sep. 2007, <URL: http://www.ptonline.com/articles/200203fa2.html>.

Legendre, Delivery of plasmid DNA into mammalian cell lines using pH-sensitive liposomes: comparison with cationic liposomes, *Pharm. Res.*, 9:1235-1242 (1992).

Loke et al., Delivery of c-myc antisense phosphorothioate oligodeoxynucleotides to hematopoietic cells in culture by liposome fusion: specific reduction in c-myc protein expression correlates with inhibition of cell growth and DNA synthesis, *Curr. Top. Microbiol. Immunol.*, 141:282-289 (1988).

Lvov et al., Nanoengineered shells for encapsulation and controlled release, pp. 1-3, *NSF Nanoscale Science and Engineering Grantees Conference* (Dec. 16-18, 2003).

Ma et al., Prevention of diabetes in NOD mice by administration of dendritic cells deficient in nuclear transcription factor kB activity. *Diabetes*, 52: 1976-85 (2003).

Machen et al., Antisense oligonucleotides down-regulating costimulation confer diabetes-preventive properties to nonobese mouse dendritic cells. *J. Immunol.* 173:4331-41 (2004).

Mahato et al., Cationic lipid-based gene delivery systems: pharmaceutical perspectives, *Pharm. Res.*, 14:853-859 (1997).

Meiri et al., Reversible antisense inhibition of Shaker-like Kv1.1 potassium channel expression impairs associative memory in mouse and rat, *Proc. Natl. Acad. Sci. USA*, 94:4430-4434 (1997).

Middaugh, Oligonucleotide delivery, In: Mathiowitz (ed.), *Encyclopedia of Controlled Drug Delivery*, vol. 2, pp. 691-697, John Wiley & Sons (1999).

Miller, Human gene therapy comes of age, *Nature*, 357:455-460 (1992).

Moghimi, Chemical camouflage of nanospheres with a poorly reactive surface: towards development of stealth and target-specific nanocarriers, *Biochimica et Biophysica Acta*, 1590:131-139 (2000).

Morita et al., Formation and isolation of spherical fine protein microparticles through lyophilization of protein-poly (ethylene glycol) aqueous mixture, *Pharm. Res.*, 17:1367-1373 (2000).

Oberhouser et al., Enhancing endosomal exit of nucleic acids using pH-sensitive viral fusion peptides, pp. 247-266, In: Akhtar (ed.), *Delivery Strategies for Antisense Oligonucleotides Therapeutics*, Boca Raton, FL: CRC Press (1995).

Pargaonkar et al., Controlled release of dexamethasone from microcapsules produced by polyelectrolyte layer by layer nanoassembly, *Pharm. Res.*, 22:826-835 (2005).

Perlaky et al., Growth inhibition of human tumor cell lines by antisense oligonucleotides designed to inhibit p120 expression, *Anti-Cancer Drug Des.*, 8:3-14 (1993).

Phillips et al., A microsphere-based vaccine prevents and reverses new-onset autoimmune diabetes. *Diabetes*, 57(6): 1544-55 (2008).

Pommersheim et al., Immobilization of enzymes by multilayer microcapsules, *Macromol. Chem. Phys.*, 195:1557-1567 (1994).

Qiu et al., Studies on the drug release properties of polysaccharide multilayers encapsulated ibuprofen microparticles, *Langmuir*, 17:5375-5380 (2001).

Radler et al., Structure of DNA-cationic liposome complexes: DNA intercalation in multilamellar membranes in distinct interhelical packing regimes, *Science*, 275:810-814 (1997).

Rashba-Step et al., Albumin microspheres as drug delivery vehicle for multiple routes of administration, *Proc. Intl. Symp. Control. Release Bioact. Mater.*, vol. 28 (2001).

Rashba-Step et al., PROMAXX protein matrix microspheres for delivery of alpha-1 antitrypsin via the pulmonary route, *Transactions 31st Annual Meeting Control. Release. Soc.*, #474 (2004).

Sah et al., Biodegradable microcapsules prepared by a w/o/w technique: effects of shear force to make a primary w/o emulsion on their morphology and protein release, *J. Microencap.*, 12:59-69 (1995).

Schwartz et al., Synthetic DNA-compacting peptides derived from human sequence enhance cationic lipid-mediated gene transfer in vitro and in vivo, *Gene Ther.*, 6:282-292 (1999).

Sinha et al., Biodegradable microspheres for protein delivery, *J. Control. Release*, 90:261-280 (2003).

Sukhorukov et al., Controlling release and permeability properties of militilayer polyelectrolyte capsules, *Proc. Intl. Symp. Control. Release Bioact. Mater.*, 28:1402-1403 (2001).

Sweeney et al., Efficient therapeutic gene delivery after systemic administration of a novel polyethylenimine/DNA vector in an orthotopic bladder cancer model, *Cancer Res.*, 63:4017-4020 (2003).

Thierry et al., Overcoming multidrug resistance in human tumor cells using free and liposomally encapsulated antisense oligodeoxynucleotides, *Biochem. Biophys. Res. Commun.*, 190:952-960 (1993).

Tiourina et al., Encapsulation of alpha chymotrypsin onto the hollow polyelectrolyte microcapsules, *Proc. Intl. Symp. Control. Release Bioact. Mater.*, 28:1400-1401 (2001).

Tiyaboonchai et al., Formulation and characterization of DNA-polyethylenimine-dextran sulfate nanoparticles, *Eur. J. Pharm. Sci.*, 19:191-202 (2003).

Tomlinson et al., Controllable gene therapy: pharmaceutics of non-viral gene delivery systems, *J. Control. Release*, 39:357-372 (1996).

Van Der Lubben et al., Chitosan microparticles for mucosal vaccination against diphtheria: oral and nasal efficacy studies in mice, *Vaccine*, 21:1400-1408 (2003).

Vanderkerken et al., Synthesis and evaluation of poly(ethylene glycol)-polylysine block copolymers as carriers for gene delivery, *J. Bioactive Compatible Polymers*, 15:115-138 (2000).

Yamakawa et al., Release behavior of poly(lactic acid-co-glycolic acid) implants containing phosphorothioate oligodeoxynucleotide, *Biol. Pharm. Bull.*, 20:455-459 (1997).

Yang et al., Novel fluorescent labels prepared by layer-to-layer assembly on colloids for biodetection systems, *Mat. Res. Soc. Symp. Proc.*, 667:G5.5.1-G5.5.6 (2001).

Yang, et al., Crystalline monoclonal antibodies for subcutaneous delivery, *Proc. Natl. Acad. Sci (USA)*, 100: 6934-6939 (2003).

Yang, et al., Layer-by-layer construction of novel biofunctional fluorescent microparticles for immunoassay applications, *J. Colloid Interface Sci.*, 234: 356-362 (2001).

Zahr et al., Fabrication of Core-Shell Drug Nanoparticles for Therapeutic Delivery, Polymeric Materials: Science & Engineering, 93: 802-803 (2005).

Zelphati et al, Mechanism of oligonucleotide release from cationic lipids, Proc. Natl. Acad. Sci (USA), 100: 11493-11498 (1996).

Zhao et al., Modulation of oligonucleotide-induced immune stimulation by cyclodextrin analogs, Biochem. Pharmacol., 52: 1537-1544 (1996).

European Supplemental Search Report, EP 04 80 9503, dated Aug. 22, 2007.

European Supplemental Search Report, EP 07 81 3820, dated Sep. 17, 2010.

International Search Report and Written Opinion of the International Searching Authority, PCT/US2004/016651, dated Feb. 14, 2005.

International Search Report and Written Opinion of the International Searching Authority, PCT/US2004/016660, dated Dec. 6, 2005.

International Search Report and Written Opinion of the International Searching Authority, PCT/US2004/023182, dated Nov. 3, 2005.

International Search Report and Written Opinion of the International Searching Authority, PCT/US2005/016689, dated Nov. 29, 2005.

International Search Report and Written Opinion of the International Searching Authority, PCT/US2006/015918, dated Sep. 18, 2006.

International Search Report and Written Opinion of the International Searching Authority, PCT/US2007/075292, dated Aug. 25, 2008.

Jinchuan et al., Upregulation of CD40-CD40 ligand system in patients with diabetes mellitus, *Clinica Chimica Acta*, 339(1-2), 85-90 (2004).

Stephens et al., Pancreatic expression of B7 co-stimulatory molecules in the non-obese diabetic mouse, *Int Immunol.*, 7(12), 1885-95 (1995).

US 5,849,884, 12/1998, Woiszwillo et al. (withdrawn)

\* cited by examiner

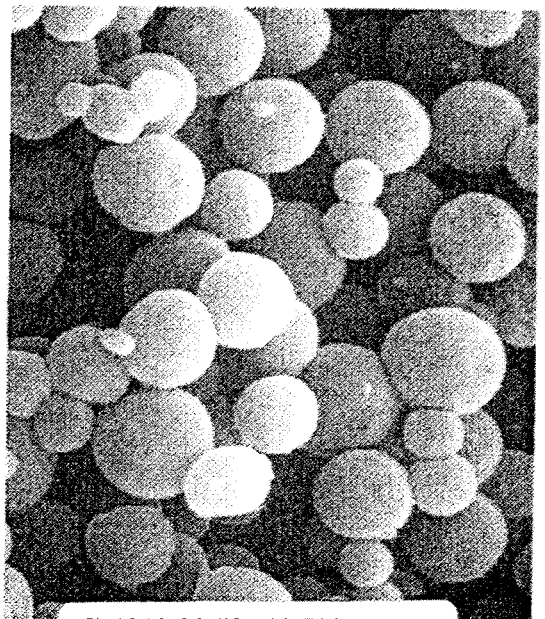 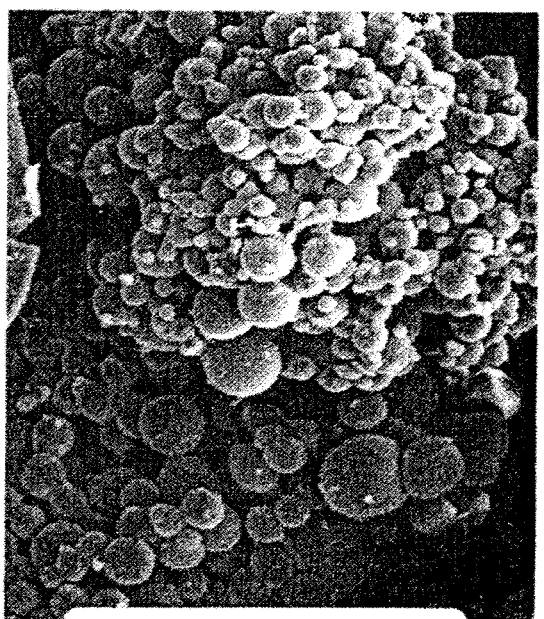
6) 1010-03 #2 x12,500
Epic Therapeutics: Oligo 2
contain L/N 1007-02-VBL
EM Center, NU 10/23/03
SEM, 10KV  1 μm
2) 1218-03 #1 x1,250
Epic Therapeutics: VBON-1215-01
EM Center, NU 12/29/03
SEM, 10KV  10 μm
FIG. 1A
FIG. 1B

Figure 6A
DIABETIC NOD
H+E
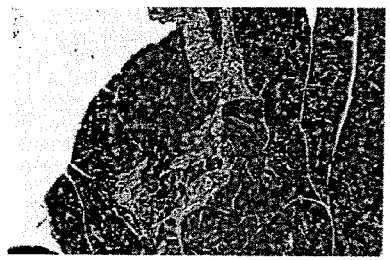
INSULIN STAINING
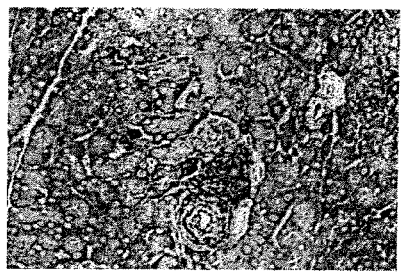
DIABETIC NOD
Figure 6B
Figure 6C
SCR-MSP NOD (HYPERGLYCEMIC)
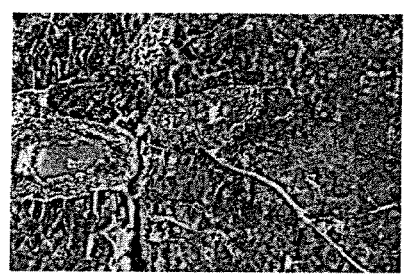
SCR-MSP NOD (HYPERGLYCEMIC)
Figure 6D

Figure 7A
ASMSP-TREATED DIABETES-FREE
NOD MICE (Tx < 8 WEEKS OF AGE)
H+E 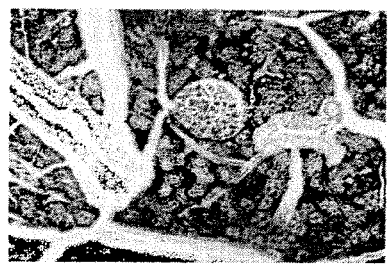
INSULIN 
Figure 7B
Figure 7C
AS-ODN DC-TREATED
DIABETES-FREE NOD MICE (Tx 10 TIMES
FOLLOWING DIABETES ONSET)
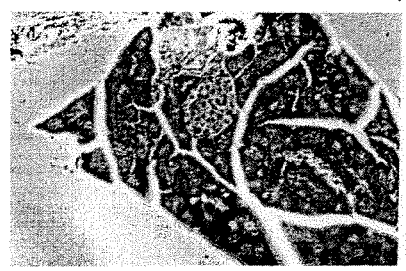
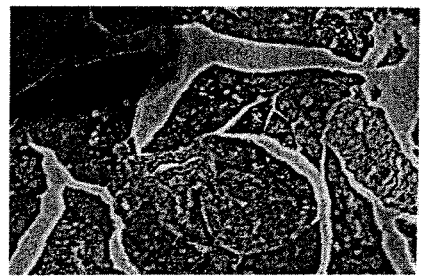
Figure 7D

GATING FOR FACS

SPLENIC T-CELLS

POOLED LYMPH NODE T-CELLS

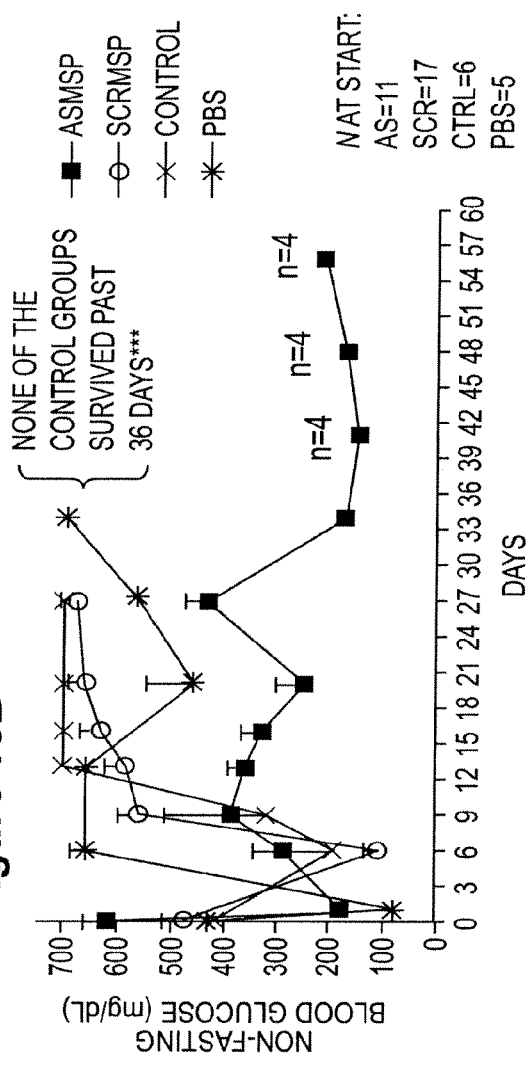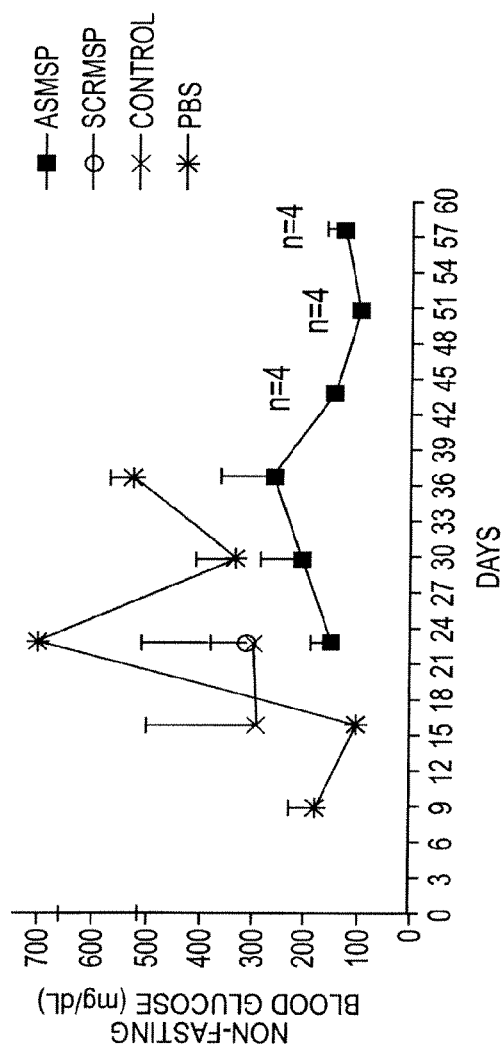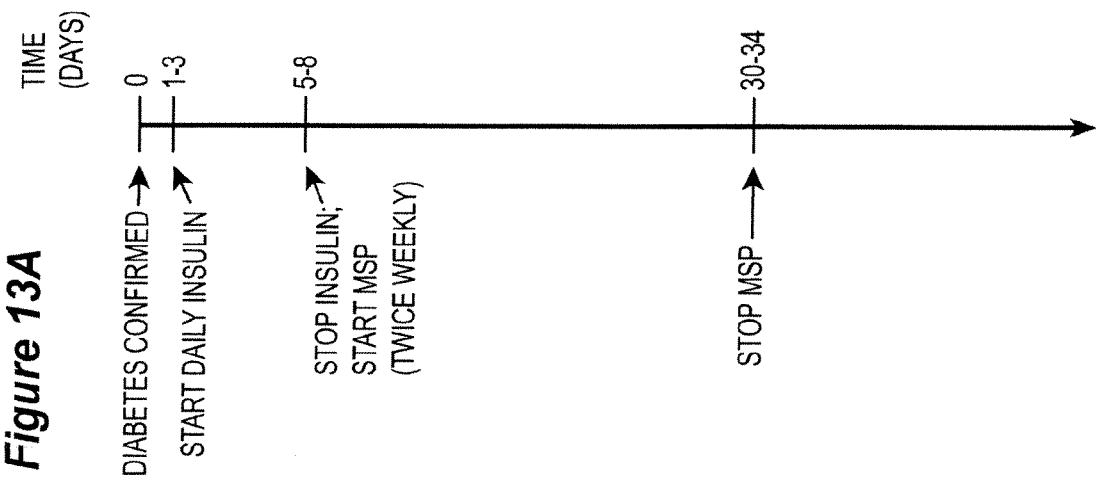

SEQUENCE LISTING

```
<160> NUMBER OF SEQ ID NOS: 3

<210> SEQ ID NO 1
<211> LENGTH: 31
<212> TYPE: DNA
<213> ORGANISM: Mus musculus

<400> SEQUENCE: 1
cacagccgag gcaaagacac catgcagggc a                                      31

<210> SEQ ID NO 2
<211> LENGTH: 29
<212> TYPE: DNA
<213> ORGANISM: Mus musculus

<400> SEQUENCE: 2
gggaaagcca ggaatctaga gccaatgga                                         29

<210> SEQ ID NO 3
<211> LENGTH: 30
<212> TYPE: DNA
<213> ORGANISM: Mus musculus

<400> SEQUENCE: 3
tgggtgcttc cgtaagttct ggaacacgtc                                        30
```

MICROSPHERE-BASED COMPOSITION FOR PREVENTING AND/OR REVERSING NEW-ONSET AUTOIMMUNE DIABETES

The present application is a divisional of U.S. patent application Ser. No. 11/834,550, filed Aug. 6, 2007, which claims the benefit of priority of U.S. Provisional Application No. 60/835,742, which was filed Aug. 4, 2006 and U.S. Provisional Application No. 60/864,914, which was filed Nov. 8, 2006. The entire text of each of the aforementioned provisional applications is incorporated herein by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "42925A_SeqListing.txt," 807 bytes, created on May 9, 2011.

BACKGROUND

The present disclosure generally relates to an antisense approach to prevent and/or reverse an autoimmune diabetes condition in NOD mice. This includes microsphere delivery of AS-oligonucleotides by injection to achieve therapeutic effect that causes a negative modulating activity, particularly in the non-obese-diabetic (NOD) mouse model. The microspheres are fabricated using totally aqueous conditions, which microspheres incorporate one or more antisense (AS) oligonucleotides.

Microparticles, microspheres, and microcapsules are solid or semi-solid particles having a diameter of less than one millimeter, and may be less than 100 microns, which can be formed of a variety of materials, including synthetic polymers, proteins, and polysaccharides. Microspheres have been used in many different applications, primarily separations, diagnostics, and drug delivery.

A number of different techniques can be used to make these particles from synthetic polymers, natural polymers, proteins and polysaccharides, including phase separation, solvent evaporation, emulsification, and spray drying. Generally the polymers form the supporting structure of these microspheres, and the drug of interest is incorporated into the polymer structure. Exemplary polymers used for the formation of microspheres include homopolymers and copolymers of lactic acid and glycolic acid (PLGA) as described in U.S. Pat. No. 5,213,812 to Ruiz, U.S. Pat. No. 5,417,986 to Reid et al., U.S. Pat. No. 4,530,840 to Tice et al., U.S. Pat. No. 4,897,268 to Tice et al., U.S. Pat. No. 5,075,109 to Tice et al., U.S. Pat. No. 5,102,872 to Singh et al., U.S. Pat. No. 5,384,133 to Boyes et al., U.S. Pat. No. 5,360,610 to Tice et al., and European Patent Application Publication Number 248,531 to Southern Research Institute; block copolymers such as such as Tetronic® 908 and poloxamer 407 as described in U.S. Pat. No. 4,904,479 to Illum; and polyphosphazenes as described in U.S. Pat. No. 5,149,543 to Cohen et al. Microspheres produced using polymers such as these exhibit a poor loading efficiency and are often only able to incorporate a small percentage of the drug of interest into the polymer structure. Therefore, substantial quantities of these types of microspheres often must be administered to achieve a therapeutic effect. In addition, these polymers typically are hydrophobic, negatively impacting the dissolution of the drug of interest. Polymers typically used in this context include polylactic glycolic acid (PLGA).

An objective for the medical community is the delivery of nucleic acids to the cells in an animal for treatment of various diseases including diabetes. In many approaches, nucleic acids can be delivered to cells in culture (in vitro) relatively efficiently with the addition of transfection agents. In addition, in vivo, the presence of endogenous nucleases results in a high rate of nucleic acid degradation when nucleic acid is delivered to animals.

In addition to protecting nucleic acid from nuclease digestion, a nucleic acid delivery vehicle must exhibit low toxicity, must be efficiently taken up by cells and have a well-defined, readily manufactured formulation. As shown in clinical trials, viral vectors for delivery can result in a severely adverse, even fatal, immune response in vivo. In addition, this method has the potential to have mutagenic effects in vivo. Delivery by complexing nucleic acids in lipid complexes of different formulations (such as liposomes or cationic lipid complexes) can have toxic effects. Complexes of nucleic acids with various polymers or with peptides have shown inconsistent results and the toxicity of these formulations has not yet been resolved. Nucleic acids also have been encapsulated in polymer matrices for delivery, but in these cases the particles have a wide size range and the effectiveness for therapeutic applications has not yet been demonstrated. Such previous approaches can yield effects that are the opposite of a goal desired herein, including stimulation of the immune system. For example, when PLGA is incorporated into particles, the immune system is stimulated by the presence of the PLGA.

Therefore, there is a need for addressing the issues in the delivery of nucleic acids, and there is an ongoing need for development of microspheres and new methods for making microspheres. Details regarding microspheres, especially details regarding their preparation and properties, are found in U.S. Pat. No. 6,458,387 to Scott et al., U.S. Pat. No. 6,268,053, U.S. Pat. No. 6,090,925, U.S. Pat. No. 5,981,719 and U.S. Pat. No. 5,599,719 to Woiszwillo et al., and U.S. Pat. No. 5,578,709 to Woiszwillo and US Patent Application Publication No. 2006/0024240 to Brown et al. These and all references identified herein are incorporated by reference hereinto.

SUMMARY

In accordance with the present disclosure, oligonucleotides are delivered as microspheres. It is believed that such a delivery approach prevents access of the nucleases to the nucleic acids within the microsphere. Microsphere delivery of antisense (AS) oligonucleotides is carried out in order to induce dendritic cell tolerance, particularly in the NOD mouse model. The microspheres are fabricated using aqueous conditions such that antisense (AS) oligonucleotides are incorporated. These microspheres are used to inhibit gene expression and to prevent and/or reverse an autoimmune diabetes condition in NOD mice in vivo.

In a one aspect of the disclosure, three AS-oligonucleotides targeted to the CD40, CD80 and CD86 transcripts are synthesized, and an aqueous solution of the oligonucleotide mixture is prepared and combined with an aqueous polymer solution. Microspheres containing the oligonucleotides are formed, and these are delivered to the NOD mice by injection.

In one aspect of the disclosure, there is provided a method for reversing type 1 diabetes in a mammal comprising administering a microsphere composition wherein microspheres in the composition comprise oligonucleotides that are antisense to and targeted to bind to primary transcripts selected from the group consisting of CD40, CD80 and CD86 primary transcripts and combinations thereof. The oligonucleotides can be selected from the group consisting of SEQ ID NO:1, SEQ ID NO:2 or SEQ ID NO:3 and combinations thereof, or indeed any other oligonucleotides that target CD40, CD80 and CD86.

Another aspect of the disclosure is directed to a method of protecting beta cells of the pancreas of a mammal from autoimmune destruction, comprising injecting into the mammal a microsphere composition, wherein the microspheres in the composition comprise oligonucleotides that are antisense to and targeted to bind to primary transcripts selected from the group consisting of CD40, CD80 and CD86 primary transcripts and combinations thereof.

Another aspect is a method of decreasing T-cell-mediated inflammation of the pancreas and/or pancreatic beta cell death in a mammal comprising administering to the mammal a microsphere composition, wherein the microspheres in the composition comprise oligonucleotides that are antisense to and targeted to bind to primary transcripts selected from the group consisting of CD40, CD80 and CD86 primary transcripts, and combinations thereof, wherein the composition is administered in an amount effective to ameliorate the symptoms of Type 1 diabetes in the mammal. In more defined aspects, the composition is administered after clinical onset of Type 1 diabetes. In alternative aspects, the composition is administered prior to clinical onset of Type 1 diabetes. In these therapeutic aspects, the administration of the composition normalizes blood glucose levels in the mammal as compared to the blood glucose levels of the mammal prior to administration.

The administration of the composition may regenerate the beta cell population of the mammal or halt the further deterioration of the beta cell population or both.

The composition may be administered in any form and in certain exemplary aspects is administered as an injectable form. In specific aspects, the composition is administered in combination with insulin. Where a combination therapy is used, the insulin may be administered prior to, concurrently with, or after administration of the microsphere composition.

Additional aspects are directed to methods of preserving residual beta cell mass in a subject with new-onset or preclinical autoimmune diabetes comprising administering to the subject a composition containing microspheres comprising oligonucleotides that are antisense to and targeted to bind to CD40, CD80 and CD86 primary transcripts, wherein administration of the composition maintains the beta cell mass of the mammal to at least about 15% of the mass present prior to diabetes onset. The subject may be a human subject. The subject may be a human child. The treatment method may involve repeated administration of the composition and the repeated administration increases the beta cell mass of the mammal.

In particular defined methods, 30% and as much as 70% w/w of the microspheres is oligonucleotide. Such compositions typically may comprise a ratio in the microsphere composition of antisense CD40:antisense CD80:antisense CD86 of 1:1:1.

These and other aspects, objects, features and advantages of the present disclosure, including the various combinations, will be apparent from and clearly understood through a consideration of the following detailed description.

BRIEF DESCRIPTION OF THE DRAWINGS

In the course of this description, reference will be made to the attached drawings, wherein:

FIGS. 1a and 1b are scanning electron micrographs of microspheres of AS-oligonucleotides and poly-L-lysine polycation.

FIG. 2a is graph showing the size distribution of a preparation of microspheres. FIG. 2b shows a graph of the surface charge of a preparation of microspheres.

FIGS. 6a-6d are light micrographs of pancreatic tissue sections from control NOD mice stained with haematoxylin and eosin (FIGS. 6 and c; H+E) or for insulin (FIGS. 6b and 6d).

FIGS. 7a-7d are light micrographs of pancreatic tissue sections from AS-MSP treated NOD mice stained with haematoxylin and eosin (FIGS. 7a and c; H+E) or for insulin (FIGS. 7b and 7d).

FIG. 13A shows a timeline for the experiments with mice having new-onset diabetes, and FIGS. 13B and 13C are plots of mean blood glucose levels from new-onset diabetic mice treated with either AS-MSP or controls.

DESCRIPTION OF THE ILLUSTRATED EMBODIMENTS

Figure 2A:
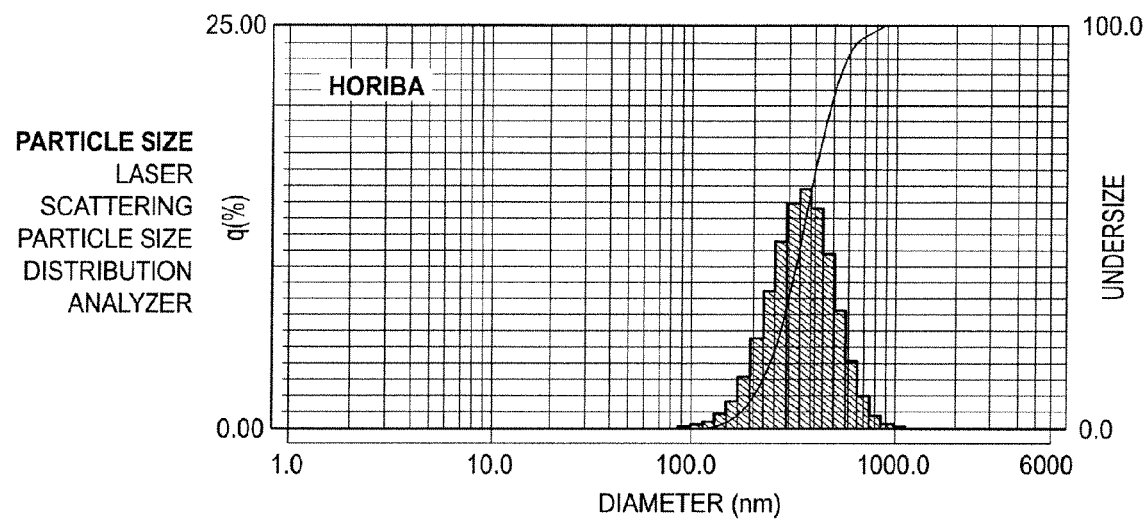
FIGS. 2a and 2b are graphs showing the properties of a microsphere preparation according to the disclosure.

As required, detailed embodiments of the present disclosure are disclosed herein; however, it is to be understood that the disclosed embodiments are merely exemplary of the disclosure, which may be embodied in various forms. Therefore, specific details disclosed herein are not to be interpreted as limiting, but merely as a basis for the claims and as a representative basis for teaching one skilled in the art to variously employ the present disclosure in virtually any appropriate manner.

Type I diabetes is an autoimmune disorder where there is a progressive inflammation of the pancreas, and specifically, the endocrine insulin-producing beta cells. Before onset, the inflammation first renders the endocrine beta cells dysfunctional. A single injection of a microsphere formulation considerably delays disease onset in the non-obese diabetic (NOD) mouse model of human autoimmune (type 1) diabetes. Although not wishing to be bound by any particular theory, it is believed the microspheres are taken up by resident and migrating dendritic cells at the site of injection and then move into the proximal lymph nodes before onset of the disease. It is also believed that a decreased proliferation of T-cells targeted to putative beta cell antigens in vitro occurs in treated recipients. An increase may occur in the prevalence of CD4+ CD25+ putative T regulatory cells in immunodeficient NOD-scid mice reconstituted with syngeneic T-cells and dendritic cells and then administered the microspheres. Thus, a microsphere-based therapeutic composition can modulate dendritic cell activity and mobilize regulatory networks for prophylaxis.

It would be desirable to have a treatment that would prevent the onset of diabetes. It would also be desirable to have a therapeutic composition that would arrest or reverse the disease after clinical onset when a substantial number of beta cells have been destroyed. Repeated administration into new-onset diabetic mice normalizes hyperglycemia and reverses the disease. Reversal typically indicates having the individual, such as a human or other mammal, exhibit near normalization of blood glucose levels. Without being bound by any particular theory, it is believed that during "reversal", disease-induced T-cell inflammation and cell death are resisted.

One embodiment reverses autoimmune insulin-dependent diabetes by formulating and injecting antisense (AS)-oligonucleotide microspheres described herein, targeting the transcripts of CD40, CD80 and CD86. Specific examples of antisense oligonucleotides directed against the transcripts are disclosed in the Examples hereof. It will be understood that other antisense oligonucleotides may be designed to be effective in binding the CD40, CD80 and CD86 transcripts to achieve the effects described herein. It will also be understood that such oligonucleotides may incorporate modifications known in the art including, but not limited to, thioation, methylation and methoxyethylation and that the location and number of such modifications may be varied to achieve an optimal effect. These oligonucleotides are designed to induce immune tolerance that results in the reversal of the destruction of the insulin producing beta cells in the NOD mouse model.

Type 1 diabetes is manifested by the autoimmune destruction of the pancreatic insulin-producing beta cells in the NOD mouse, as well as in humans. At the time of clinical onset, humans typically have 10-20% or less of residual beta cell mass. Sparing of any of this residual mass can result in remaining insulin levels which are adequate to regulate glucose levels. In addition, reversing the destruction of beta cells may result in the partial regeneration of the beta cell population. The oligonucleotide-containing microparticles of the present disclosure are provided to interfere with the autoimmune destruction of the beta cells.

It will be appreciated that dendritic cells (DC) can be activated to be potent antigen-presenting cells found in all tissues and which are present under the skin. These antigen-presenting dendritic cells function as triggers of the immune response, including autoimmune responses, through the activation of T-cells, particularly in lymph nodes. Although not wishing to be bound by theory, CD40, CD80 and CD86 are believed to be important for the autoimmune response, and the downregulation of these molecules is thought to promote autoimmune hyporesponsiveness. In addition, certain cytokines, such as interferons and interleukins, are reduced as a result of the hyporesponsiveness.

In making the microspheres that are used for treatment of autoimmune diabetes in mice, one, two or three AS-oligonucleotides may be dissolved in aqueous solution and combined with water soluble polymer(s) and a polycation. The solution typically is incubated at about 60-70° C., cooled to about 23° C., and the excess polymer is removed.

The nucleic acids typically comprise between about 30 and about 100 weight percent of the microspheres and have an average particle size of not greater than about 50 microns, typically not greater than about 20 microns, and can be not more than about 10 microns. Typically, they are prepared as follows. An aqueous solution of the oligonucleotide or oligonucleotides is prepared. When microspheres containing three oligonucleotides are to be prepared, aliquots from three oligonucleotide solutions are combined. Each solution contains one of these three oligonucleotide types. The final solution containing oligonucleotides typically contains about 10 mg/ml of oligonucleotide.

In specific examples, the microsphere formulation contains 65%, 70%, 75%, 80%, 85%, 90% w/w or greater load of oligonucleotides. In such embodiments, the compositions have a poly-L-lysine content of 6-10% w/w. in addition the moisture content of the microspheres varies and can be approximately 4%. The oligonucleotides are present in a ratio of 1:1:1 of antisense CD40:antisense CD80:antisense CD86.

These are combined with aliquots of a 10 mg/ml stock solution of polycation. Examples of polycations are polylysine and poly-ornithine. Others include polyethyleneimine (PEI), prolamine, protamine, polyvinyl pyrrolidone (PVP), polyarginine, vinylamine, and derivatives of positively-charged polysaccharides, such as positively charged chitosan, and combinations thereof. The polycation solution can be at volumetric ratios of polycation:oligonucleotide of from about 1:1 to about 4:1. Commonly used polycations include poly-L-lysine.HBr (up to 70,000 Daltons available from Bachem) and poly-L-ornithine.HBr (e.g. 11,900 Daltons available from Sigma).

Polymer solutions also are prepared. These can function as phase-separation enhancing agents. Examples of suitable polymers include linear or branched polymers, copolymers and block copolymers. These polymers can be water soluble, semi-water soluble, water-miscible, or soluble in a water-miscible solvent. Examples of polymers include pharmaceutically acceptable additives such as polyethylene glycol (PEG) of various molecular weights, such as PEG 200, PEG 300, PEG 3350, PEG 8000, PEG 10000, PEG 20000, etc. and poloxamers of various molecular weights such as poloxamer 188 and Pluronic FI27 or Pluronic F68. A commonly used polymer is polyvinylpyrrolidone (PVP). Another polymer is hydroxyethylstarch. Other amphiphilic polymers can also be used alone or in combinations. The phase-separation enhancing agent can also be a non-polymer such as a mixture of propylene glycol and ethanol.

In a typical embodiment, a polymer solution of polyvinyl pyrrolidone and/or of polyethylene glycol may be prepared and combined with the other solutions. Heating, cooling, centrifuging and washing multiple times provide an aqueous suspension which typically is frozen and lyophilized to form a dry powder of microspheres comprising oligonucleotide and polycation.

The microspheres are suitable for in vivo delivery by an injectable route, including intravenous, intramuscular, subcutaneous, intraperitoneal, intrathecal, epidural, intra-arterial, intra-articular and the like. Other delivery routes that can be practiced include such as topical, oral, rectal, nasal, pulmonary, vaginal, buccal, sublingual, transdermal, transmucosal, otic or intraocular.

Without being bound by any particular theory, it is believed that microspheres containing the antisense oligonucleotides exemplified herein down-regulate cell surface molecules CD40, CD80 and CD86. The microspheres are injected and dendritic cells are believed to actively uptake the oligonucleotide microspheres. These oligonucleotides suppress the expression of cell surface cell molecules CD40, CD80 and CD86 in dendritic cells. The administration of these antisense oligonucleotide microspheres after development in the NOD mouse effectively reverses diabetes.

The following Examples illustrate certain features and advantages of the disclosure in order to further illustrate the disclosure. The Examples are not to be considered limiting or otherwise restrictive of the disclosure.

Example 1

Three AS-oligonucleotides targeted to the CD40, CD80 and CD86 primary transcripts were synthesized. The AS-oligonucleotide sequences used in this Example are, with asterisks indicating sites of thioation in the backbone:

```
Seq ID 1:
CD 40-AS:   5'C*AC* AG*C C*GA* GG*C* AA*A
            GA*C* AC*C A*T*G C*AG* GG*C* A-3'

Seq ID 2:
CD80-AS:    5'-G*GG* AA*A G*CC* AG*G A*AT* CT*A
            G*AG* CC*A A*TG G*A-3'

Seq ID 3:
CD86-AS:    5'-T*GG* GT*G C*TT* CC*G T*AA*
            GT*T C*TG* GA*A C*AC* G*T*C_3'
```

An aqueous solution of the oligonucleotide mixture was prepared by combining aliquots of three oligonucleotide solutions, each of which contained one type of oligonucleotide, to form a 10 mg/ml solution of the three types of oligonucleotides. A 10 mg/ml solution of poly-L-lysine.HBr in deionized water (poly-L-lysine.HBr up to 70,000 Daltons, by Bachem, King of Prussia, Pa.) was prepared. The poly-L-lysine.HBr was added to the oligonucleotides solution at a volumetric ratio of 1:1. The mixture was vortexed gently. A 25% polymer solution containing 12.5% PVP (polyvinyl pyrrolidone, 40,000 Daltons, Spectrum Chemicals, Gardena, Calif.) and 12.5% PEG (polyethylene glycol, 3,350 Daltons, Spectrum Chemicals, Gardena, Calif.) in 1M Sodium Acetate (Spectrum, Gardena, Calif.) at pH5.5 was added in a 2:1 volumetric ratio as follows: 0.75 ml of AS-oligonucleotides, 0.75 ml of poly-L-lysine.HBr, 3.0 ml of PEG/PVP, and a total volume of 4.50 ml.

The batch was incubated for 30 minutes at 70° C. and then cooled to 23° C. Upon cooling, the solution became turbid and microspheres were formed. The suspension was then centrifuged, and the excess PEG/PVP was removed. The resulting pellet was washed by resuspending the pellet in deionized water, followed by centrifugation and removal of the supernatant. The washing process was repeated three times. The aqueous suspension was frozen and lyophilized to form a dry powder of microspheres comprising oligonucleotide and poly-L-lysine.

Figure 2B:
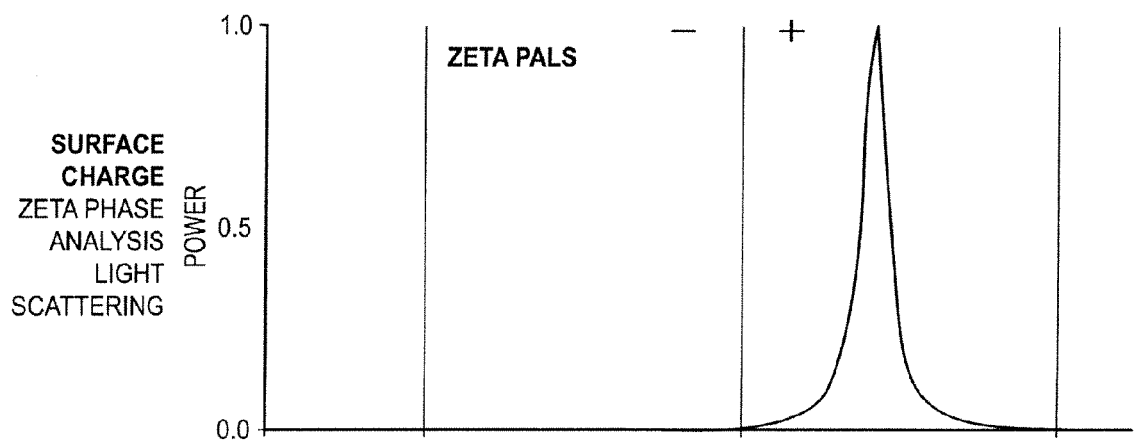
Figure 3:
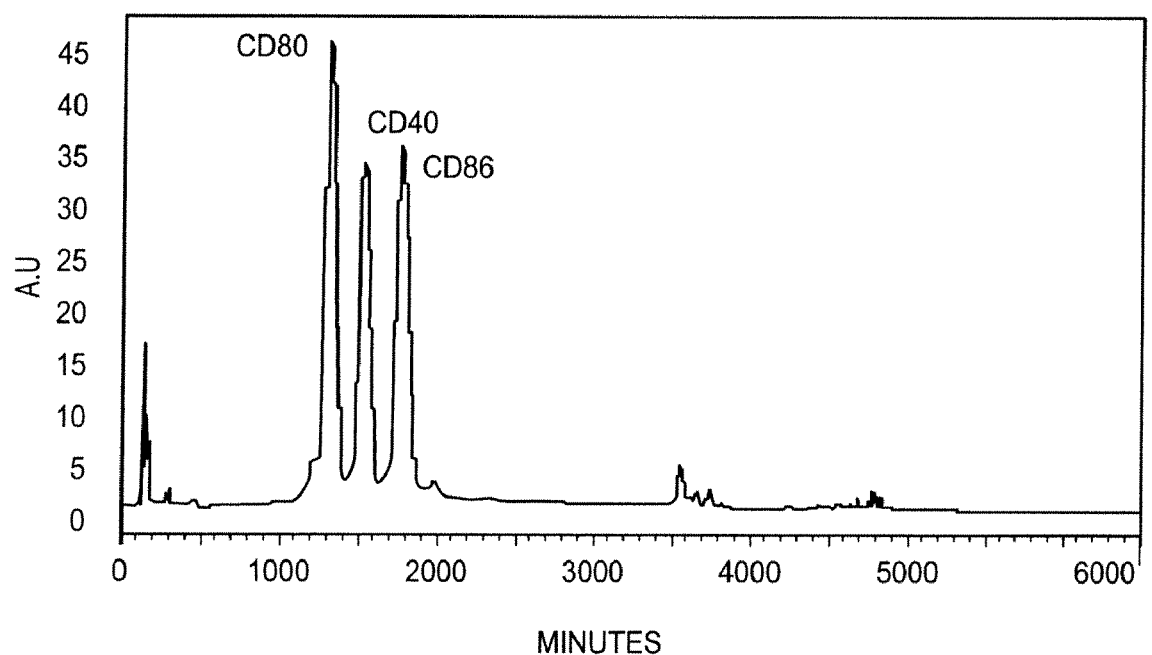
FIG. 3 is a RP-HPLC chromatogram of the oligonucleotides after deformulation of microspheres.

FIGS. 1a and b present representative scanning electron micrographs (SEM) of 1:1 poly-L-lysine:oligonucleotide ratio microspheres at two different magnifications. Microspheres, 0.5-4 µm in size, with an average particle size of approximately 2.5 µm were fabricated. FIG. 2a shows the size distribution of one preparation of microspheres made according to the disclosure as revealed by laser light scattering. FIG. 2b shows the determination of the surface charge of a microsphere preparation (Zeta potential) by light scattering. FIG. 3 shows a reverse phase (RP) HPLC method used to quantitate the loading and assess the integrity of the antisense oligonucleotide components of the microspheres after deformulation. Microspheres were formulated using CD86, CD40, CD80 oligonucleotides and poly-L-lysine (PLL; MW 30-70 kD). The microspheres were then deformulated using competitive displacement of the DNA oligonucleotides from the PLL by poly-L-aspartic acid (PAA). PAA was selected as a polyamino acid reagent that does not absorb at 260 nm and does not interfere with quantification of oligonucleotides at 260 nm. In RP-HPLC profiles such as FIG. 3, the area under each peak is proportional to amount of each oligonucleotide loaded into the microsphere. As shown in FIG. 3, the peak heights indicate approximately equal loading of each oligonucleotide into microspheres. The loading of oligonucleotides into microspheres was calculated to be from about 65% to about 80% by weight. FIG. 3 also shows that the integrity of the oligonucleotides was not affected by the microsphere formulation process, as indicated by the narrow distribution of the peaks after deformulation.

Example 2

Figure 4:
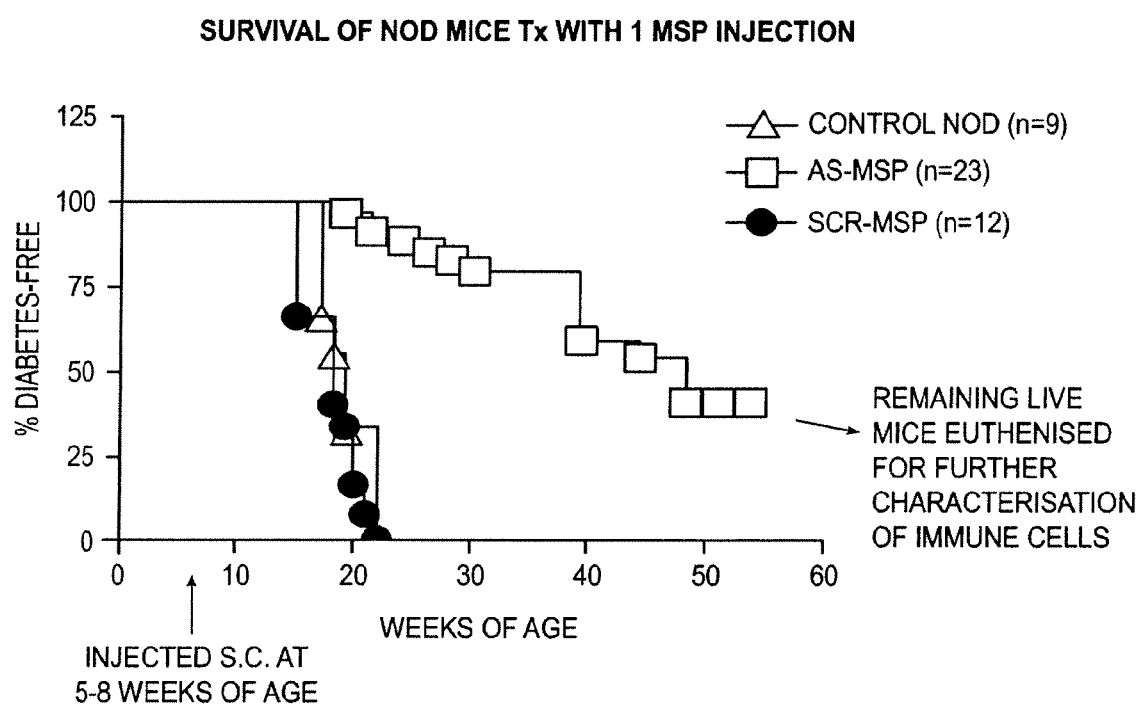
FIG. 4 is a plot showing the prevention of diabetes in NOD mice treated multiple times with antisense oligonucleotide microspheres (AS-MSP) of the disclosure compared to animals treated with scrambled oligonucleotides microspheres or with the PBS vehicle alone.

In this Example, the results of tests that cover prevention aspects of the disclosure are shown. As shown in FIG. 4, a single AS-MSP administration into NOD mice at 5-8 weeks of age delays diabetes onset. Two groups of NOD female mice (5-8 weeks old) were given a single subcutaneous injection of antisense-oligonucleotides formulated into microspheres of the disclosure (AS-MSP). The formulation was injected in injected in an amount considered to contain 50 µg of a 1:1:1 mixture of each antisense oligonucleotide (anti-CD40, anti-CD80 and anti-CD86). Other groups of mice were injected with scrambled sequence microspheres (SCR-MSP) or PBS vehicle (control NOD). Blood glucose was measured weekly via tail vein puncture. Diabetes was confirmed after two consecutive readings of >280-300 mg/dL. FIG. 4 shows the cumulative survival of two independently-treated cohorts.

Figure 5:
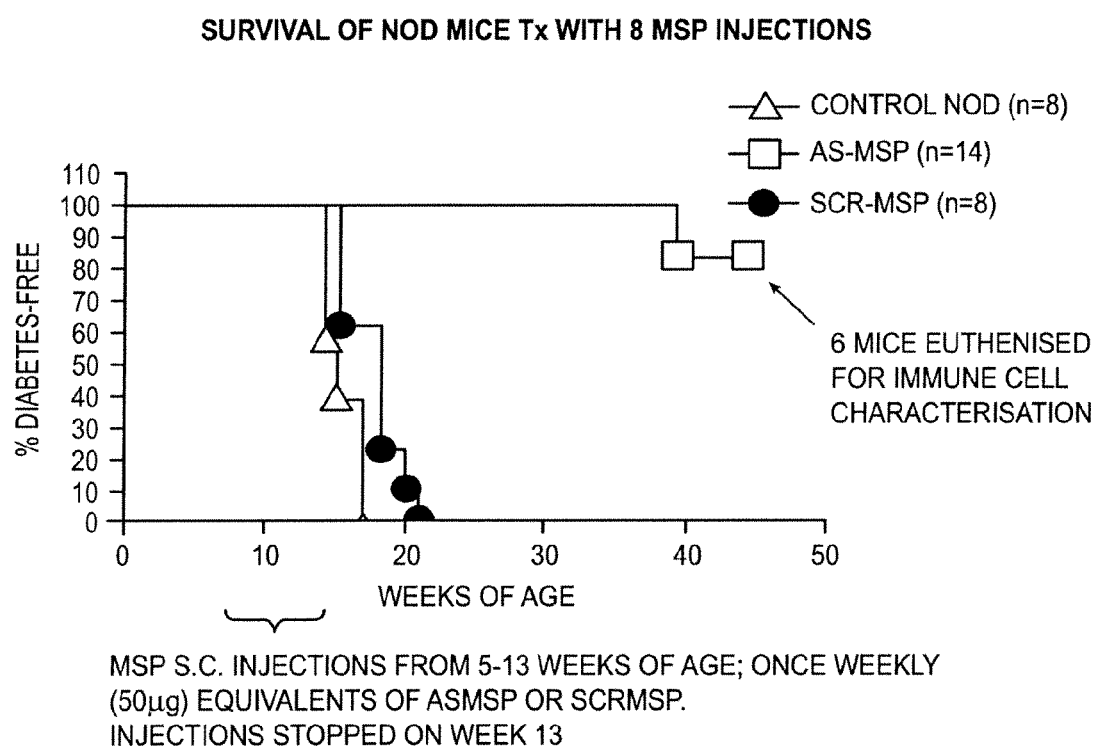
FIG. 5 is a plot showing the prevention of diabetes in NOD mice treated once with AS-MSP of the disclosure compared to animals treated with scrambled oligonucleotide microspheres or with the PBS vehicle alone.

FIG. 5 shows that multiple AS-MSP administration into NOD mice at 5-8 weeks of age prevents diabetes onset. NOD female mice (5-8 weeks old) were given eight consecutive single subcutaneous injections (once weekly) of antisense oligonucleotide formulated into microspheres according to the disclosure. Injections (50 µg of a 1:1:1 mixture of each antisense oligonucleotides or scrambled oligonucleotides) were given once weekly for eight weeks and stopped at week 13. Other groups of mice were injected with scrambled sequence microspheres (SCR-MSP) or PBS vehicle (control NOD). FIG. 5 shows the cumulative survival of treated animals.

FIGS. 6a and 6b show sections of pancreatic tissue from mice that received no treatment and thus progress spontaneously to autoimmunity (diabetic NOD mice) stained with haematoxylin and eosin (H+E; FIG. 6a) or stained for insulin (FIG. 6b). FIGS. 6c and 6d show sections of pancreatic tissue from mice treated with SCR-MSP formulations (injections started in parallel with the groups treated with specific AS-MSP). These sections were also stained with haematoxylin and eosin (H+E; FIG. 6c) or stained for insulin (FIG. 6d). The SCR-MSP mice all developed diabetes.

FIGS. 7a and 7b shows sections of pancreatic tissue from mice treated when less than 8 weeks of age (prevention model) and treated with the antisense microspheres of the disclosure stained with haematoxylin and eosin (H+E; FIG. 7a) or stained for insulin (FIG. 7b).

Figure 8A:
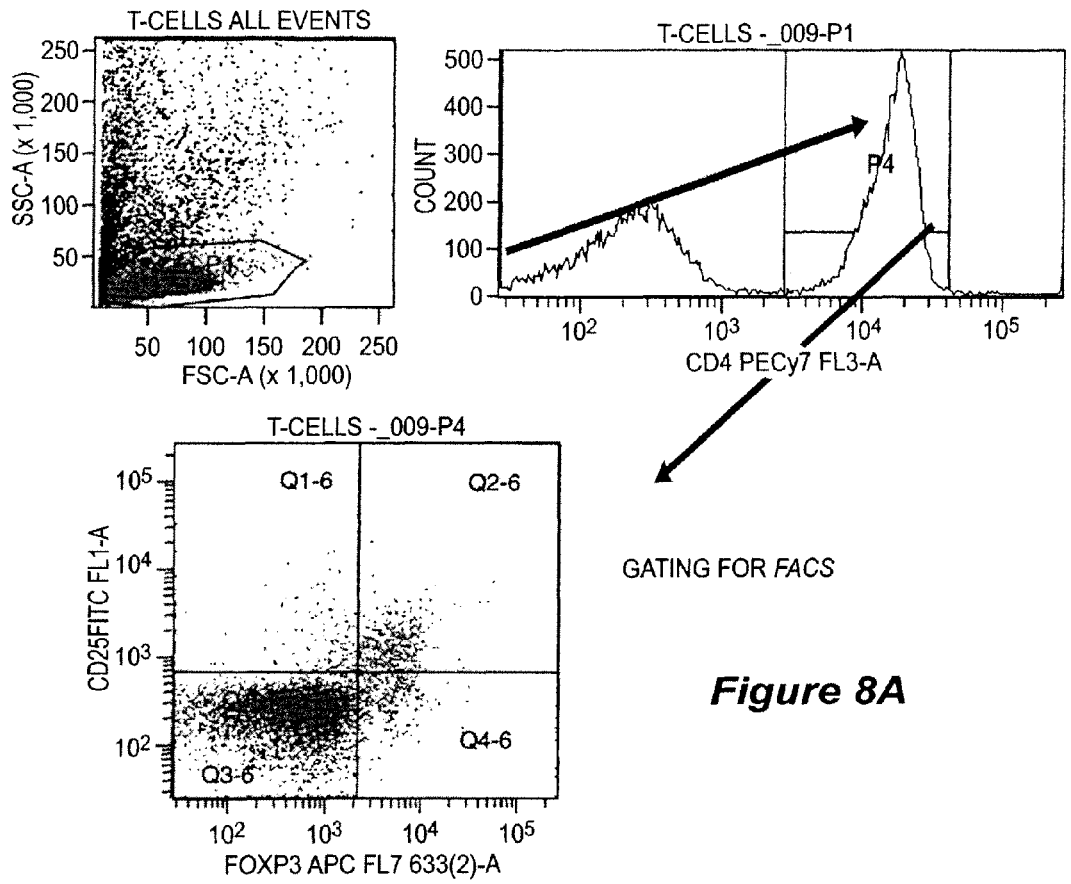
FIG. 8 shows a FACS analysis of T cells obtained from mice treated with the AS-MSP of the disclosure or from control animals.
Figure 8B:
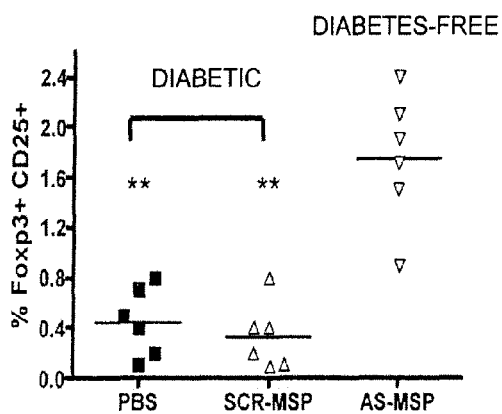
Figure 8C:
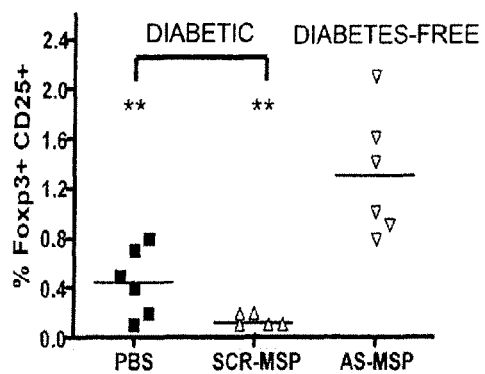

As shown in FIG. 8, T-cells from AS-MSP treated, NOD mice exhibit increased prevalence of Foxp3+ CD25+ putative $T_{reg}$ cells. FIG. 8A shows the gating used for FACS analysis. FIG. 8B shows percentages of Foxp3+ CD25+ T-cells that were enriched from the spleen and FIG. 8C the percentages from the pooled lymph nodes for ASMSP-treated diabetes-free mice selected at random from the ASMSP diabetes-free cohort or from or from animals treated with scrambled sequence microspheres (SCR-MSP) or treated with PBS vehicle.

Figure 9A:
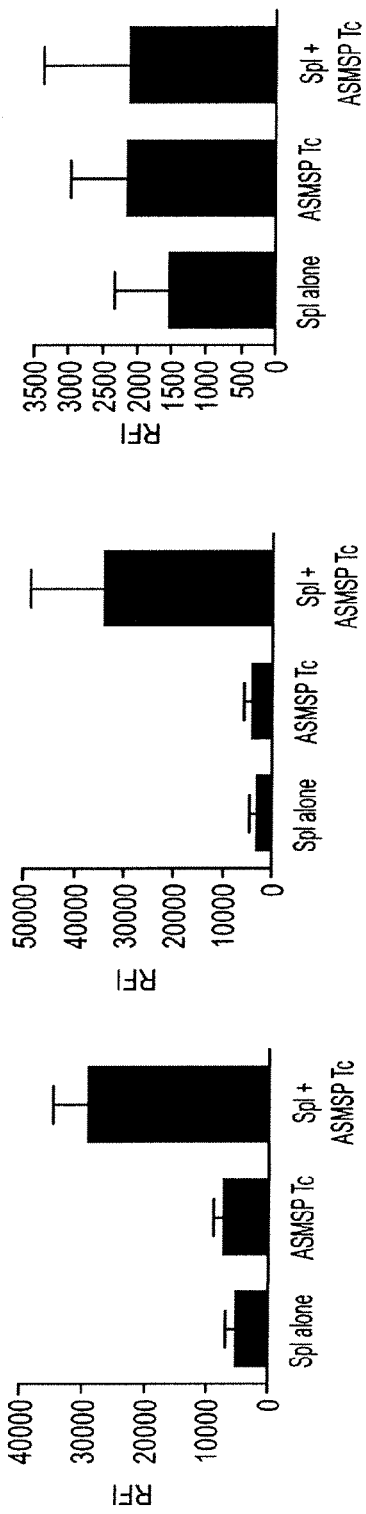
FIG. 9 shows plots of relative fluorescent intensity (RFI) demonstrating the proliferation of T cells from animals treated with AS-MSP and cultured with splenocytes according to the disclosure.
Figure 9B:
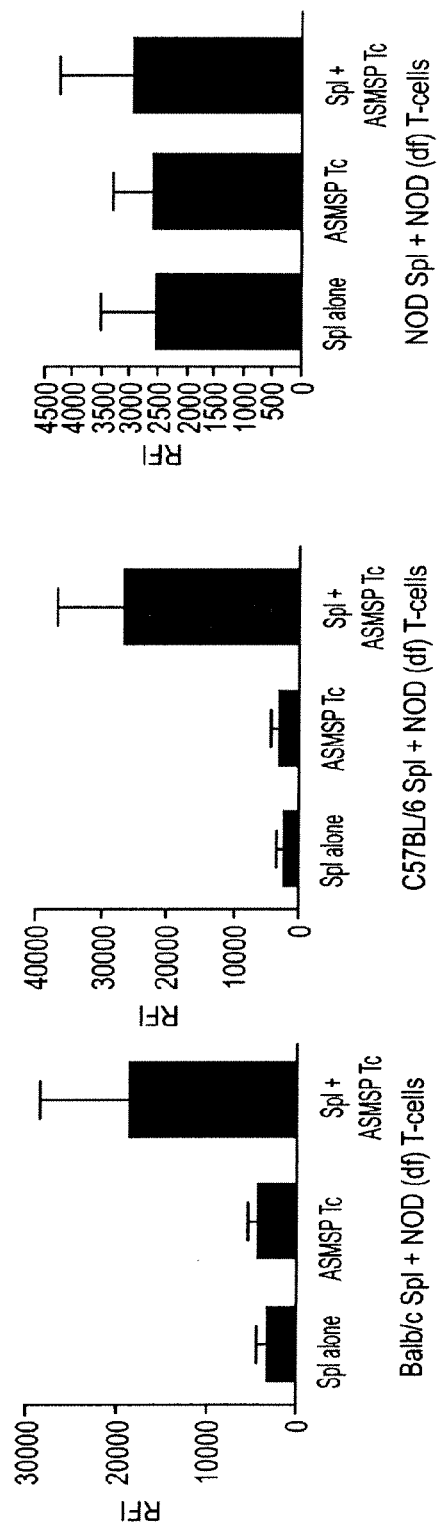

FIG. 9 shows that T-cells from ASMSP-treated diabetes-free NOD mice proliferate when co-cultured with allogeneic splenocytes. T-cells from diabetes-free NOD mice treated with ASMSP were obtained over enrichment columns and co-cultured with γ-irradiated splenocytes from Balb/c, C57BL6 or syngeneic diabetes-free NOD mice (10 weeks of age). Proliferation was measured four days later using the Cyquant reagent. Spl refers to allogeneic irradiated splenocytes.

Figure 10A:
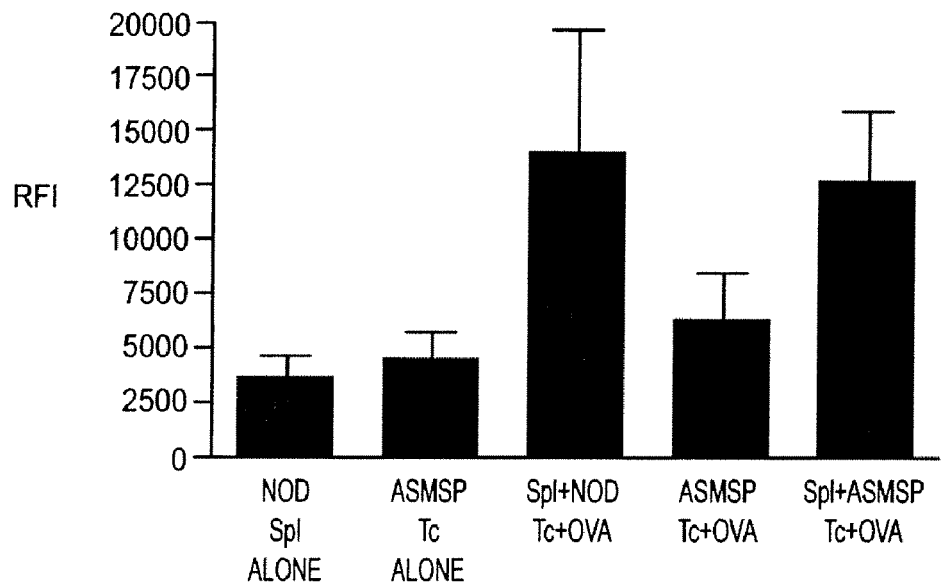
FIG. 10 shows plots of RFI demonstrating the proliferation of T-cells from AS-MSP treated, diabetes-free NOD mice in the presence of syngeneic irradiated splenocytes and ovalbumin in vitro.
Figure 10B:
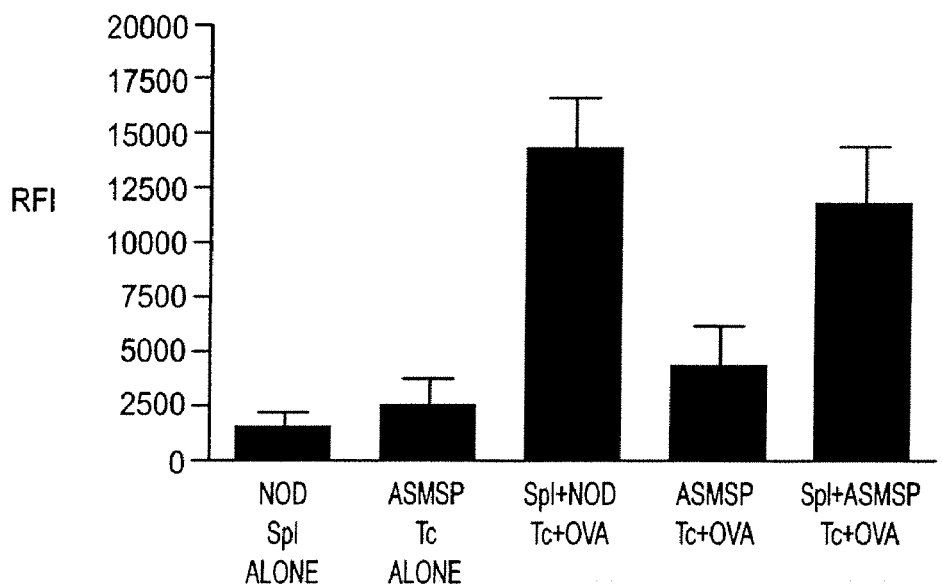

As shown in FIG. 10, T-cells from ASMSP-treated, diabetes-free NOD mice proliferate in the presence of syngeneic irradiated splenocytes and ovalbumin in vitro. T-cells were enriched from the spleen or the pooled lymph nodes of ASMSP-treated diabetes-free mice selected at random from the ASMSP diabetes-free cohort.

Figure 11A:
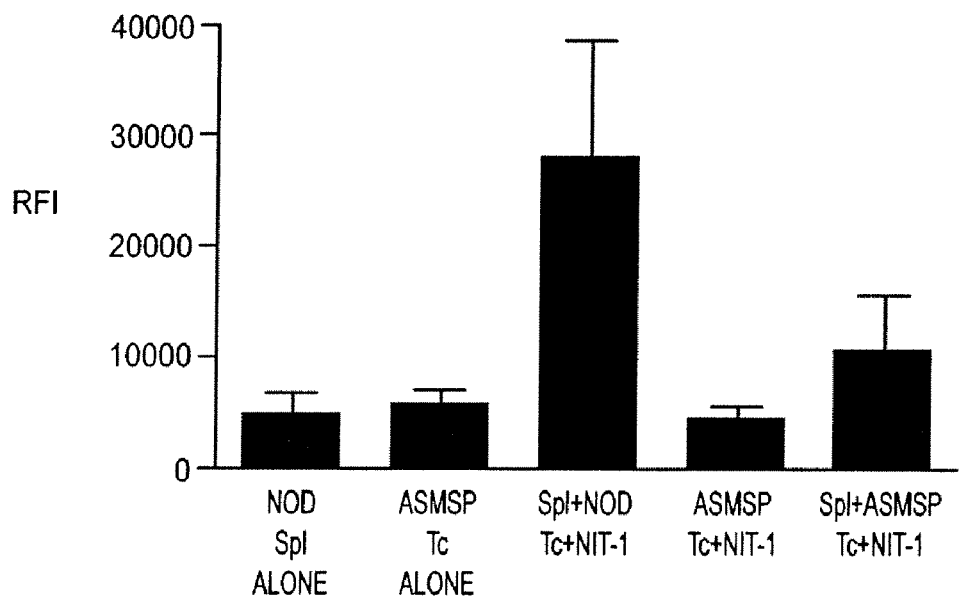
FIG. 11 shows plots of RFI demonstrating the suppressed proliferation of T-cells from AS-MSP-treated, diabetes-free NOD mice in the presence of syngeneic islet lysate in vitro.
Figure 11B:
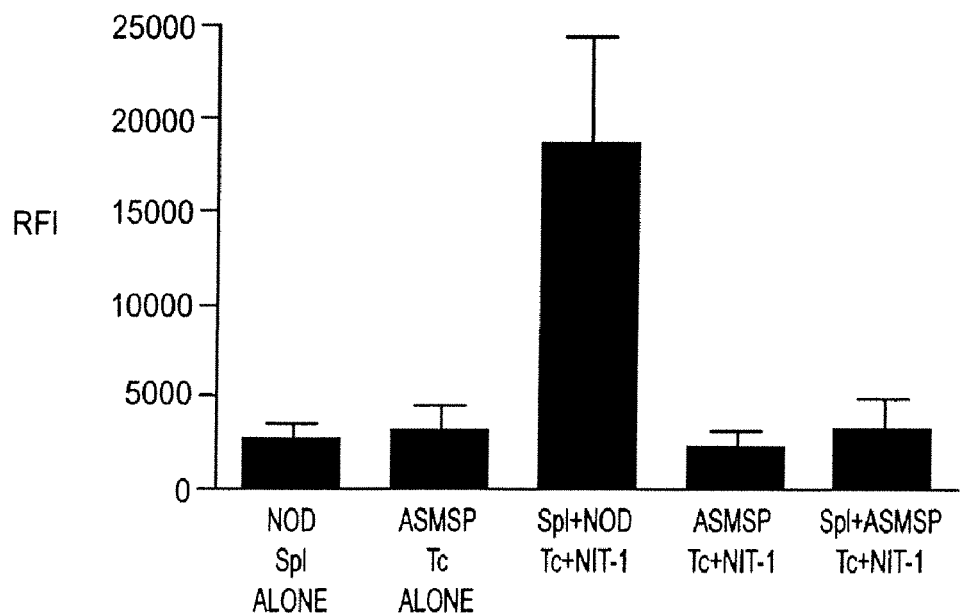

FIG. 11 shows that T-cells from ASMSP-treated, diabetes-free NOD mice exhibit suppressed proliferation in the presence of syngeneic islet lysate in vitro. T-cells were enriched from the spleen or the pooled lymph nodes of ASMSP-treated diabetes-free mice selected at random from the ASMSP diabetes-free cohort as described in FIG. 4. Irradiated NOD splenocytes (from diabetes-free 10 week-old NOD mice) were used as antigen-presenting cells and parallel cultures were pulsed with NIT-1 lysate (1 µg/well)(or PBS vehicle).

A major concern for eventual translation of diabetes-suppressive therapies into human trials is the antigen specificity (and therefore the cell specificity) of the treatment approach and whether the treatment confers global and non-specific suppression. To address these issues, randomly-selected diabetes-free mice were euthanized from the cohorts shown in FIG. 4 to ascertain the proliferation of splenic and lymph node T-cells to alloantigen, nominal antigen (in the form of intact ovalbumin) and to syngeneic beta cell-derived antigen in the form of cell lysate from the NOD derived insulinoma cell line NIT-1. While insulin and glutamic acid decarboxylase (GAD) are viable candidate autoantigens with mechanistic and teleologic involvement, the nature of the initiating autoantigen remains unclear. Nevertheless, it is reasonable to consider that it should be beta-cell resident. Therefore, the NIT-1 cell line which derives from an NOD insulinoma was used as a source of beta cell antigen in cocultures of T-cells from diabetes-free NOD mice treated with the AS-MSP to determine the possibility of antigen-specific hyporesponsiveness. From these studies, it was seen that T-cell proliferation to nominal and alloantigen is maintained whereas there is T-cell hypoproliferation in cocultures with NIT-1 cell lysate.

Furthermore, ascertaining the cytokine profile in the co-culture supernatants, we observed a significant decrease in TNFα production by T-cells from AS-MSP-treated, diabetes-free NOD mice even in the presence of NIT-1 lysate. Although IFNγ production was slightly decreased in the co-cultures of T-cells from the AS-MSP-treated mice, it was not statistically-distinguishable from the co-cultures with T-cells from PBS-treated mice in the presence of NIT-1 lysate. The assay, finally, could not detect the presence of IL-4, IL-10 or TGFβ in the supernatants.

Example 3

Figure 12A:
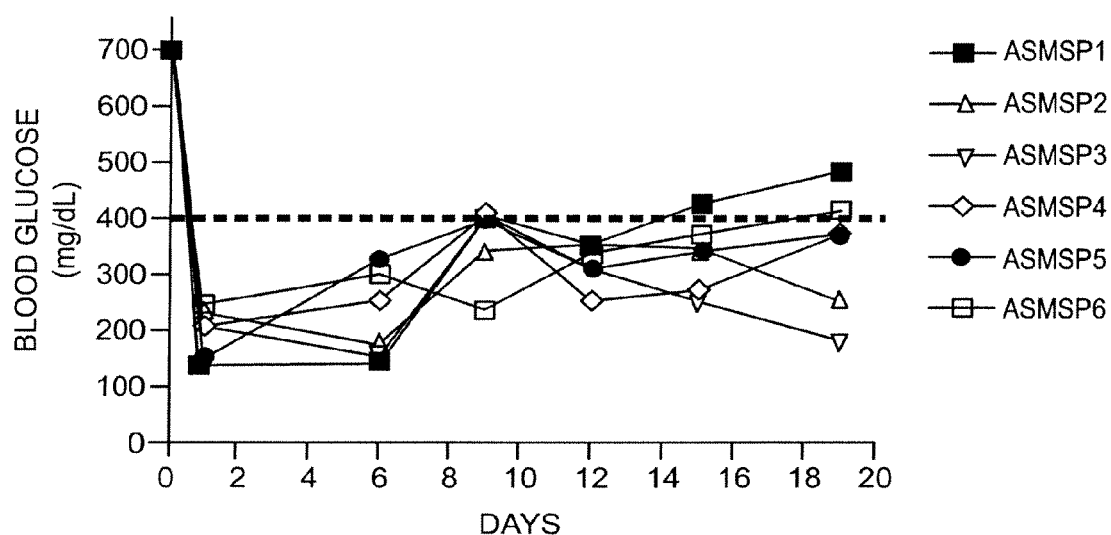
FIG. 12 is a plot of blood glucose levels from new-onset diabetic mice treated with either microspheres containing antisense or scrambled oligonucleotides.
Figure 12B:
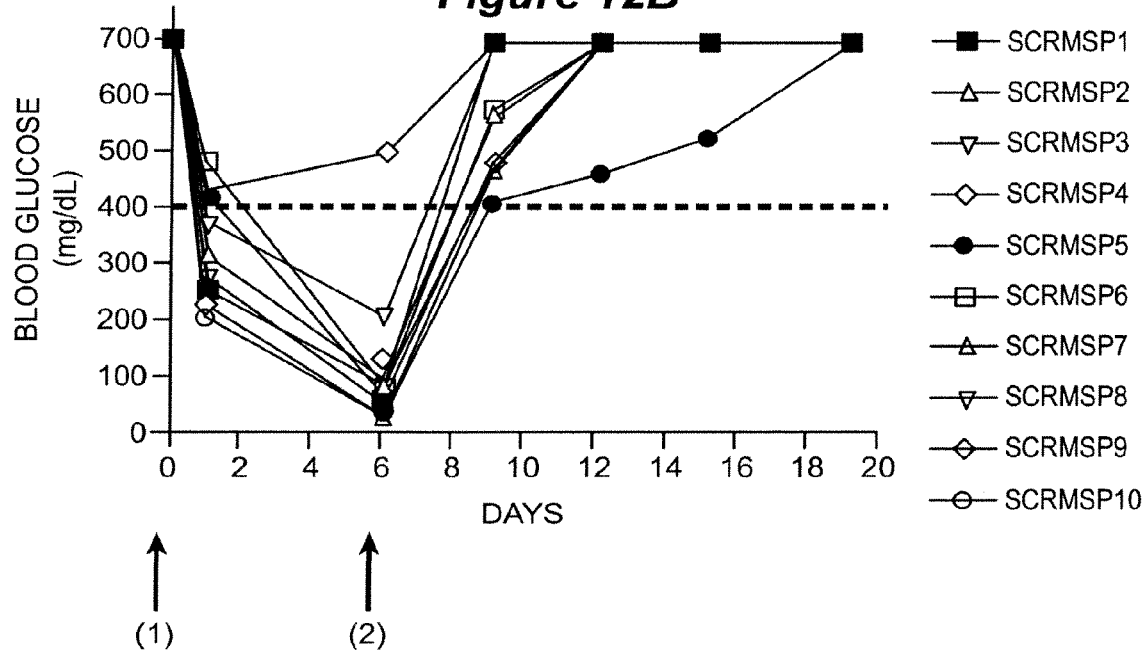

The ability of antisense oligonucleotide microspheres to reverse the symptoms of diabetes in early onset NOD mice was also tested. A timeline for these experiments is shown in FIG. 13A. NOD mice that had early onset were selected by testing blood glucose levels and identifying animals that had a blood glucose level greater than 400 mg/dL. The selected animals were given insulin pellets to normalize blood glucose levels to below 300 mg/dL. The insulin was withdrawn and a series of parenteral injections of microspheres was started. Six animals were injected twice weekly with microspheres containing the CD40, CD80 and CD86 antisense oligonucleotides. A further ten animals were injected with microspheres containing a mixture of oligonucleotides with scrambled sequences that are not directed against CD40, CD80 and/or CD86. Each injection for both groups of animals contained 50 of oligonucleotides in microspheres in 100 microliters of injection solution. Two of the animals in the scrambled group were euthanized before the end of the experiment due to poor physical condition. After the commencement of the injection protocol, blood glucose levels were sampled twice weekly. The animals were non-fasting during the experiment. The results are plotted in FIG. 12, wherein the indicator (1) signifies insulin pellet installation and indicator (2) signifies insulin pellet removal and initiation of MSP injections twice weekly. It is noted that the maximum blood glucose value reported in FIG. 12 is 700 mg/dL, which corresponds to the maximum reading of the meter used, it being understood that a 700 mg/dL data point indicates a blood glucose reading of 700 mg/dL or higher, All animals in the group that received the microspheres containing the mixture of CD40, CD80, CD86 antisense oligonucleotides (ASMSP1 through ASMSP6) showed significantly lower glucose levels than the animals that received the microspheres with scrambled oligonucleotides (SCRMSP1 through SCRMSP10). Furthermore, four of six animals in this ASMSP group showed a blood glucose level below 400 mg/dL, typically considered to be a threshold indicator of diabetes onset.

In FIG. 13A, the timeline for the experiments is shown. The mean non-fasting blood glucose (FIG. 13B) and the mean fasting blood glucose levels for each group are plotted (FIG. 13C) (+/−SEM). In some mice, ASMSP administration was withdrawn as shown in FIG. 13A. As shown in FIGS. 13B and 13C, multiple rounds of AS-MSP administration into new-onset diabetic NOD female mice improves blood glucose levels and result in stable fasting euglycemia even after AS-MSP withdrawal relative to untreated animals (control), animals treated with PBS or animals treated with scrambled oligonucleotides (SCR-MSP) microspheres.

FIGS. 7c and 7d show sections of pancreatic tissue from NOD mice that were treated with antisense formulations after onset of diabetes and showed reversal of the disease. The sections are stained with haemotoxylin and eosin (H+E; FIG. 7c) or stained for insulin (FIG. 7d).

3 different AS-oligonucleotides can be incorporated into PROMAXX microspheres and such microspheres can be used as a composition to prevent and/or reverse new onset autoimmune diabetes via immunoregulatory dendritic cell induction. Indeed, a single injection of the composition delayed disease onset and repeated administration into new-onset diabetic mice normalized hyperglycemia, suggesting reversal of disease. In these studies, insulin was administered daily until blood glucose fell below 300 mg/dL. Insulin then was stopped whereupon AS-MSP were administered subcutaneously. In an exemplary dosing regiment, the animals were administered 2 mg AS-MP per kg body weight two times a week for 3-4 weeks. The diabetes-free NOD mice were monitored.

Figure 14A:
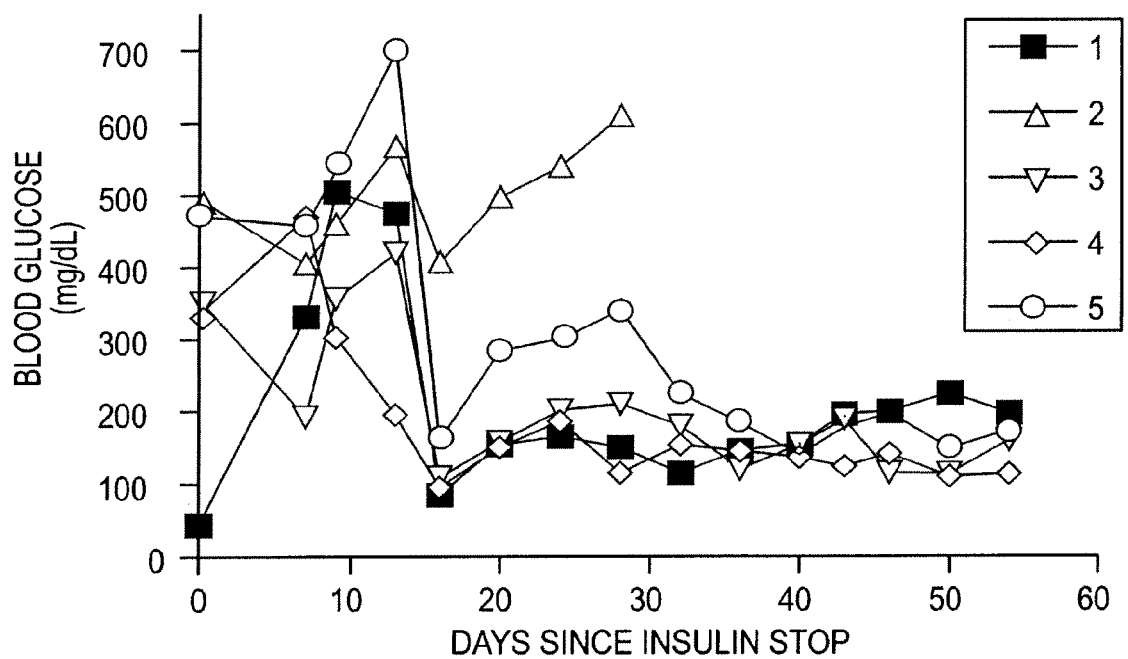
FIG. 14A-C shows reversal of the type-1 diabetes phenotype in NOD mice. These figures show that upon administration of AS-MSP the blood glucose levels of the mammals return to normal within 15 days (normal levels are shown by the dashed line at approx 200 mg/dL) and remain at normal even after AS-MSP administration is stopped (day 30).
Figure 14B:
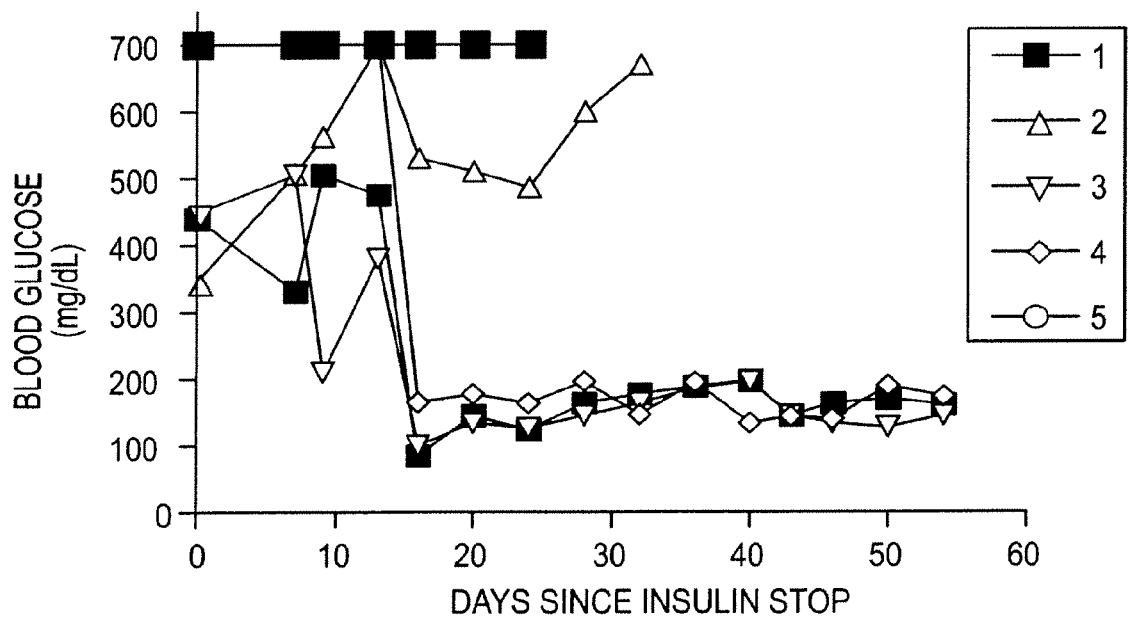
Figure 14C:
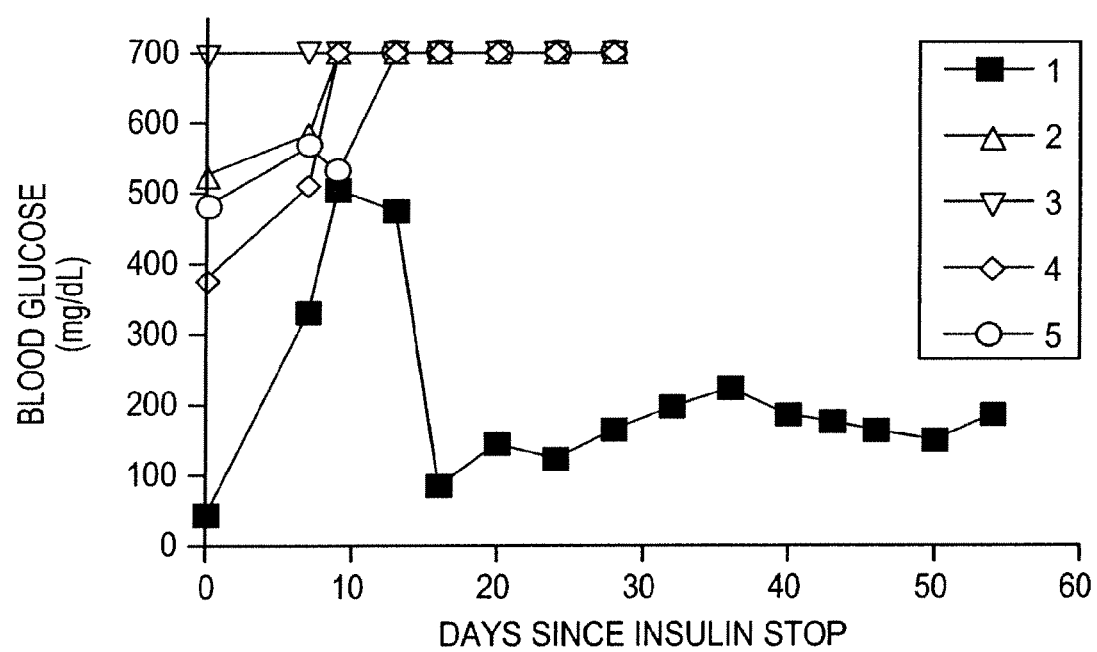

In FIG. 14A-C it is demonstrated that administration of AS-MSP to NOD mice returns the blood glucose levels of said mice to normal levels and the normalization of said blood glucose level is maintained for an extended period of time. As shown in FIGS. 14B and 14C, AS-MSP was administered between days 0-30 after insulin administration was stopped. The blood glucose level returned to normal by day 15 post insulin stop and remained at a normal level until the end of the monitoring period (day 55).

Figure 15:
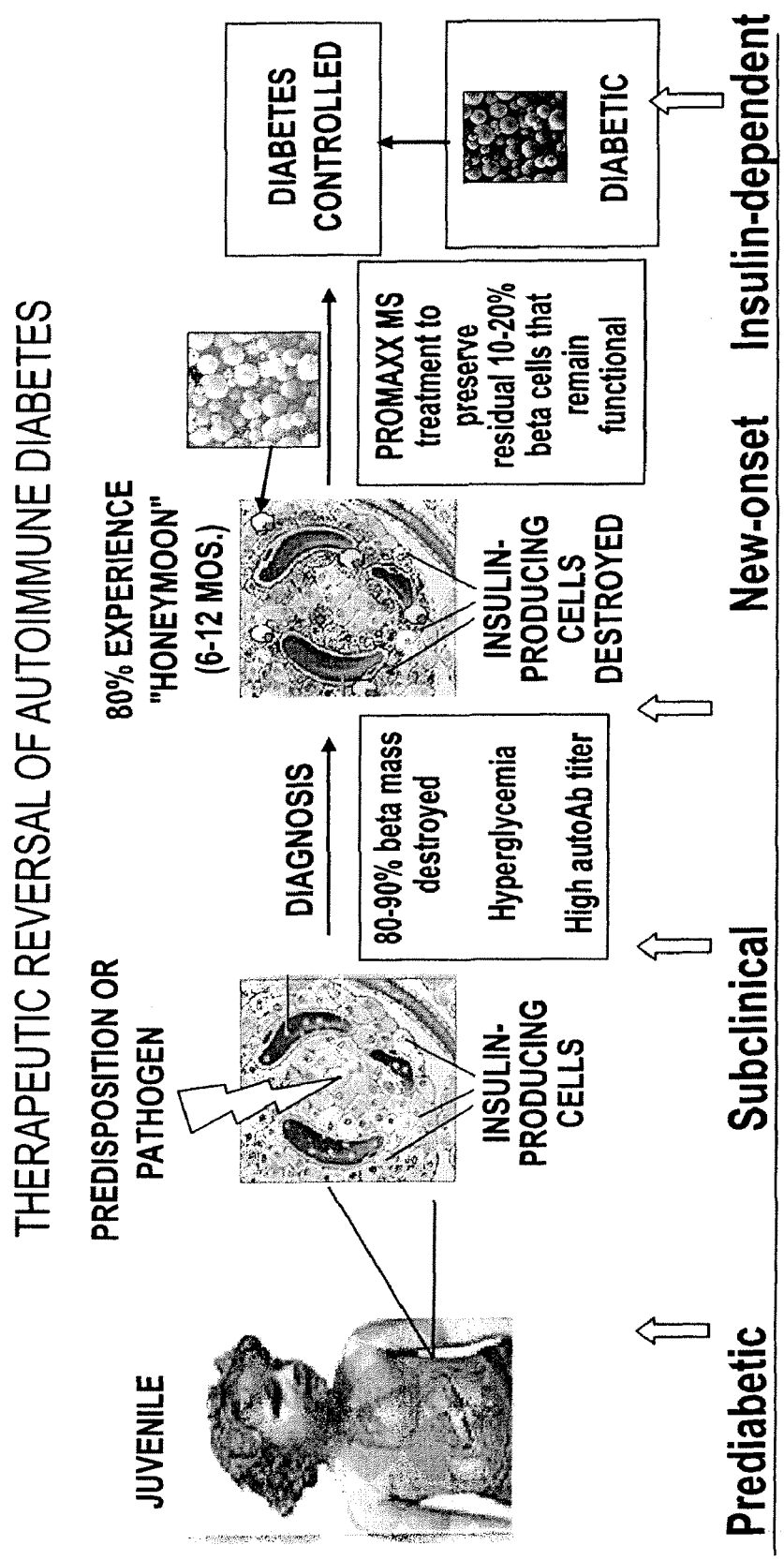
FIG. 15 Model depicting therapeutic reversal of autoimmune diabetes.

A diagram showing the impact of therapeutic reversal of autoimmune diabetes is show in FIG. 15. If PROMAXX treatment were administered at the new onset "honeymoon" shown in FIG. 15, it is predicted that there would be a preservation of the 10-20% beta cells that remain functional, thereby leading to a control of the diabetes and reducing the dependence of the patient on insulin.

It will be understood that the embodiments of the present disclosure which have been described are illustrative of some of the applications of the principles of the present disclosure. Numerous modifications may be made by those skilled in the art without departing from the true spirit and scope of the disclosure. Various features which are described herein can be used in any combination and are not limited to precise combinations which are specifically outlined herein.

The invention claimed is:

1. A method of decreasing T-cell-mediated inflammation of the pancreas in a mammal comprising administering to said mammal a microsphere composition, wherein microspheres in said composition comprise oligonucleotides that are antisense to and targeted to bind to primary transcripts selected from the group consisting of CD40, CD80 and CD86 primary transcripts, and combinations thereof, wherein said composition is administered in an amount effective to ameliorate the symptoms of Type I diabetes in said mammal.

2. The method of claim 1, wherein said composition is administered after clinical onset of Type 1 diabetes.

3. The method of claim 1, wherein said composition is administered prior to clinical onset of Type 1 diabetes.

4. The method of claim 1, wherein administration of said composition normalizes blood glucose levels in said mammal as compared to the blood glucose levels of said mammal prior to administration.

5. The method of claim 1, wherein said method comprises administration of a composition containing microspheres that comprising oligonucleotides that are antisense to and targeted to bind to CD40, CD80 and CD86 primary transcripts.

6. The method of claim 1, wherein said composition is administered as an injectable form.

7. The method of claim 1, wherein said composition is administered in combination with insulin.

8. The method of claim 7, wherein said insulin is administered prior to, concurrently with, or after administration of said microsphere composition.

9. The method of claim 1, wherein 70% w/w of said microspheres is oligonucleotide.

10. The method of claim 9, wherein the ratio in said microsphere composition of antisense CD40:antisense CD80: antisense CD86 is 1:1:1.

* * * * *